United States Patent
Caranta et al.

(10) Patent No.: US 7,919,677 B2
(45) Date of Patent: Apr. 5, 2011

(54) EIF4E GENE MUTATIONS AND POTYVIRUS RESISTANCE

(75) Inventors: Carole Caranta, Caumont-sur-Durance (FR); Sandrine Ruffel, St Clément de Riviere (FR); Abdelhafid Bendahmane, Le Coudray Montceaux (FR); Alain Palloix, Le Thor (FR); Christophe Robaglia, Venelles (FR)

(73) Assignee: Genoplante-Valor, Evry (FR)

( * ) Notice: Subject to any disclaimer, the term of this patent is extended or adjusted under 35 U.S.C. 154(b) by 281 days.

(21) Appl. No.: 10/502,795

(22) PCT Filed: Feb. 7, 2003

(86) PCT No.: PCT/FR03/00397
§ 371 (c)(1),
(2), (4) Date: Jun. 9, 2005

(87) PCT Pub. No.: WO03/066900
PCT Pub. Date: Aug. 14, 2003

(65) Prior Publication Data
US 2005/0255455 A1 Nov. 17, 2005

(30) Foreign Application Priority Data

Feb. 8, 2002 (FR) ..................................... 02 01583
Oct. 31, 2002 (FR) ..................................... 02 13678

(51) Int. Cl.
*C12N 15/09* (2006.01)
*C12N 15/82* (2006.01)
*A01H 1/00* (2006.01)
*C12Q 1/68* (2006.01)
*C12Q 1/70* (2006.01)

(52) U.S. Cl. ........ 800/278; 800/279; 800/298; 800/317; 800/280; 435/5; 435/6

(58) Field of Classification Search .................. None
See application file for complete search history.

(56) References Cited

FOREIGN PATENT DOCUMENTS
WO 99 43820 9/1999
WO 01 40490 6/2001

OTHER PUBLICATIONS

Ruffel et al. Mol. Gen Genomics (2005) 274:346-353.*
Whitman, S. et al. "Selectable viruses and altered susceptibility mutants in *Arabidopsis thaliana*" Proc. Natl. Acad. Sci. USA, vol. 96, pp. 772-777 Jan. 1999.
Leonard, Simon et al. "Complex Formation between Potyvirus VPg and Translation Eukaryotic Initiation Factor 4E Correlates with Virus Infectivity" Journal of Virology, The American Society for Microbiology, US, vol. 74, No. 17, pp. 7730-7737 Sep. 2000.
Revers, F. et al. "New Advances In Understanding the Molecular Biology of Plant/Potyvirus Interactions" Molecular Plant-Microbe Interactions, APS Press, St. Paul, MN, US, vol. 12, No. 5, pp. 367-376 1999.
Lellis, A. et al. "Loss-of-Susceptibility Mutants of *Arabidopsis thaliana* Reveal an Essential Role for eIF(iso)4E during Potyvirus Infection" Current Biology, vol. 12, No. 12, pp. 1046-1051 Jun. 25, 2002.

* cited by examiner

*Primary Examiner* — Medina A Ibrahim
(74) *Attorney, Agent, or Firm* — Oblon, Spivak, McClelland, Maier & Neustadt, L.L.P.

(57) ABSTRACT

The invention concerns a method for obtaining potyvirus resistant plants exhibiting one or several mutations in a preserved region of the eIF4E translation factor, defined by the following general sequence (I):
$DX_1X_2X_3X_4KSX_5QX_6AWGSSX_7RX_8X_9YTFSX_{10}VEX_{11}FWX_{12}X_{13}YNNIHX_{14}P\ SKLX_{15}X_{16}GAD$ wherein: —$X_1$, $X_2$, $X_3$, $X_4$, $X_6$, $X_7$, $X_8$, $X_9$, $X_{10}$, $X_{12}$, $X_{13}$, $X_{15}$, et $X_{16}$ represent each a neutral amino acid; $X_5$ and $X_{14}$ represent a basic amino acid; $X_{11}$ represents an acid amino acid; D, K, S, Q, A, W, G, R, Y, T, F, V, E, N, I, H, P, and L have their usual one-letter code meaning.

24 Claims, 3 Drawing Sheets

| | |
|---|---|
| YW | MATAEMEKTTTFDEAEKVKLNANEADDEVEEGEIVEETDDTTSYLSKEIATKHPLEHSWT |
| DDL | MATAEMEKTTTFDEAEKVKLNANEADDEVEEGEIVEETDDTTSYLSKEIATKHPLEHSWT |
| PM1008 | MATAEMEKTTTFDEAEKVKLNANEADDEVEEGEIVEETDDTTSYLSKEIATKHPLEHSWT |
| YY | MATAEMEKTTTFDEAEKVKLNANEADDEVEEGEIVEETDDTTSYLSKEIATKHPLEHSWT |
| Avelar | MATAEMEKTTTFDEAEKVKLNANEADDEVEEGEIVEETDDTTSYLSKEIATKHPLEHSWT |
| Vania | MATAEMEKTTTFDEAEKVKLNANEADDEVEEGEIVEETDDTTSYLSKEIATKHPLEHSWT |
| PM994 | MATAEMEKTTTFDEAEKVKLNANEADDEVEEGEIVEETDDTTSYLSKEIATKHPLEHSWT |
| Florida | MATAEMEKTTTFDEAEKVKLNANEADDEVEEGEIVEETDDTTSYLSKEIATKHPLEHSWT |
| C69 | MATAEMEKTTTFDEAEKVKLNANEADDEVEEGEIVEETDDTTSYLSKEIATKHPLEHSWT |
| CM334 | MATAEMEKTTTFDEAEKVKLNANEADDEVEEGEIVEETDDTTSYLSKEIATKHPLEHSWT |
| PM1014 | MATAEMEKTTTFDEAEKVKLNANEADDEVEEGEIVEETDDTTSYLSKEIATKHPLEHSWT |
| Per | MATAEMEKTTTFDEAEKVKLNANEADDEVEEGEIVEETDDTTSYLSKEIATKHPLEHSWT |
| | ************************************************************ |

| | |
|---|---|
| YW | FWFDNPVAKSKQAAWGSSLRNVYTFSTVEDFWGAYNNIHHPSKLVVGADLHCFKHKIEPK |
| DDL | FWFDNPVAKSKQAAWGSSLRNVYTFSTVEDFWGAYNNIHHPSKLVVGADLHCFKHKIEPK |
| PM1008 | FWFDNPVEKSKQDDWGSSLRNVYTFSTVEDFWGAYNNIHHPSKLVVGADLHCFKHKIEPK |
| YY | FWFDNPEAKSKQAAWGSSRRNVYTFSTVEDFWGAYNNIHHPSKLVVGADLHCFKHKIEPK |
| Avelar | FWFDNPEAKSKQAAWGSSRRNVYTFSTVEDFWGAYNNIHHPSKLVVGADLHCFKHKIEPK |
| Vania | FWFDNPEAKSKQAAWGSSRRNVYTFSTVEDFWGAYNNIHHPSKLVVGADLHCFKHKIEPK |
| PM994 | FWFDNPEAKSKQAAWGSSRRNVYTFSTVEDFWGAYNNIHHPSKLVVGADLHCFKHKIEPK |
| Florida | FWFDNPEAKSKQAAWGSSLRNVYTFSTVEDFWGAYNNIHHPSKLVVGANLHCFKHKIEPK |
| C69 | FWFDNPEAKSKQAAWGSSLRNVYTFSTVEDFWGAYNNIHHPSKLVVGADLHCFKHKIEPK |
| CM334 | FWFDNPEAKSKQAAWGSSLRNVYTFSTVEDFWGAYNNIHHPSKLVVGADLHCFKHKIEPK |
| PM1014 | FWFDNPEAKSKQAAWGSSLRNVYTFSTVEDFWGAYNNIHHPSKLVVGADLHCFKHKIEPK |
| Per | FWFDNPEAKSKQAAWGSSLRNVYTFSTVEDFWGAYNNIHHPSKLVVGADLHCFKHKIEPK |
| | ****   ******************************:********* |

| | |
|---|---|
| YW | WEDPVCANGGTWKMSFSKGKSDTSWLYTLLAMIGHQFDHEDEICGAVVSVRGKGEKISLW |
| DDL | WEDPVCANGGTWKMSFSKGKSDTSWLYTLLAMIGHQFDHEDEICGAVVSVRGKGEKISLW |
| PM1008 | WEDPVCANGGTWKMSFSKGKSDTSWLYTLLAMIGHQFDHEDEICGAVVSVRGKGEKISLW |
| YY | WEDPVCANGGTWKMSFSKGKSDTSWLYTLLAMIGHQFDHEDEICGAVVSVRGKGEKISLW |
| Avelar | WEDPVCANGGTWKMSFSKGKSDTSWLYTLLAMIGHQFDHEDEICGAVVSVRGKGEKISLW |
| Vania | WEDPVCANGGTWKMSFSKGKSDTSWLYTLLAMIGHQFDHEDEICGAVVSVRGKGEKISLW |
| PM994 | WEDPVCANGGTWKMSFSKGKSDTSWLYTLLAMIGHQFDHEDEICGAVVSVRGKGEKISLW |
| Florida | WEDPVCANGGTWKMSFSKGKSDTSWLYTLLAMIGHQFDHEDEICGAVVSVRGKGEKISLW |
| C69 | WEDPVCANGGTWKMSFSKGKSDTSWLYTLLAMIGHQFDHEDEICGAVVSVRGKGEKISLW |
| CM334 | WEDPVCANGGTWKMSFSKGKSDTSWLYTLLAMIGHQFDHEDEICGAVVSVRGKGEKISLW |
| PM1014 | WEDPVCANGGTWKMSFSKGKSDTSWLYTLLAMIGHQFDHEDEICGAVVSVRGKGEKISLW |
| Per | WEDPVCANGGTWKMSFSKGKSDTSWLYTLLAMIGHQFDHEDEICGAVVSVRGKGEKISLW |
| | ************************************************************ |

| | |
|---|---|
| YW | TKNAANETAQVSIGKQWKQFLDYSDSVGFIFHDDAKRLDRNAKNRYTV |
| DDL | TKNAANETAQVSIGKQWKQFLDYSDSVGFIFHDDAKRLDRNAKNRYTV |
| PM1008 | TKNAANETAQVSIGKQWKQFLDYSGSVGFIFHDDAKRLDRNAKNRYTV |
| YY | TKNAANETAQVSIGKQWKQFLDYSDSVGFIFHDDAKRLDRNAKNRYTV |
| Avelar | TKNAANETAQVSIGKQWKQFLDYSDSVGFIFHDDAKRLDRNAKNRYTV |
| Vania | TKNAANETAQVSIGKQWKQFLDYSDSVGFIFHDDAKRLDRNAKNRYTV |
| PM994 | TKNAANETAQVSIGKQWKQFLDYSDSVGFIFHDDAKRLDRNAKNRYTV |
| Florida | TKNAANETAQVSIGKQWKQFLDYSDSVGFIFHDDAKRLDRNAKNRYTV |
| C69 | TKNAANETAQVSIGKQWKQFLDYSGSVGFIFHDDAKRLDRNAKNRYTV |
| CM334 | TKNAANETAQVSIGKQWKQFLDYSGSVGFIFHDDAKRLDRNAKNRYTV |
| PM1014 | TKNAANETAQVSIGKQWKQFLDYSGSVGFIFHDDAKRLDRNAKNRYTV |
| Per | TKNAANETAQVSIGKQWKQFLDYSGSVGFIFHDDAKRLDRNAKNRYTV |
| | *********************.********************* |

Fig 3

```
Mospo  MAAAEMERTMSFDAAEKLKAADGGGGEVDDELEEGEIVEESNDTASYLGKEITVKHPLEH
PI13   MAAAEMERTMSFDAAEKLKAADGGGGEVDDELEEGEIVEESNDTASYLGKEITVKHPLEH
PI24   MAAAEMERTMSFDAAEKLKAADGGGGEVDDELEEGEIVEESNDTASYFGKEITVKHPLEH Mospo  SWTFWFDNPTTKSRQTAWGSSLRNVYTFSTVEDFWGAYNNIHHPSKLIMGADFHCFKHKI
PI13   SWTFWFDNSTTKSRQTAWGSSLRNLYTFSTVEDFWGAYNNIHHPSKLIMGADFHCFKHKI
PI24   SWTFWFDKSTTKSRQTDWGSSLRNLYTFSTVEDFWGAYNNIHHPSKLIIGADFHCFKHKI Mospo  EPKWEDPVCANGGTWKMSFSKGKSDTSWLYTLLAMIGHQFDHGDEICGAVVSVRAKGEKI
PI13   EPQWEDPVCANGGTWKMSFSKGKSDTSWLYTLLAMIGHQFDHGDEICGAVVSVRAKGEKI
PI24   EPQWEDPVCANGGTWKMSFSKGKSDTSWLYTLLAMIGHQFDHGDEICGAVVSVRAKGEKI Mospo  ALWTKNAANETAQVSIGKQWKQFLDYSDSVGFIFHDDAKRLDRNALNRYTV
PI13   ALWTKNAANETAQVSIGKQWKQFLDYSDSVGFIFHDDAKRLDRSALNRYTV
PI24   ALWTKNAANETAQVSIGKQWKQFLDYSDSVGFIFHDDAKRLDRSALNRYTV
```

FIG. 4

```
SEQUENCE LISTING

<160> NUMBER OF SEQ ID NOS: 36

<210> SEQ ID NO 1
<211> LENGTH: 46
<212> TYPE: PRT
<213> ORGANISM: Artificial Sequence
<220> FEATURE:
<223> OTHER INFORMATION: Consensus DNA Sequence
<220> FEATURE:
<221> NAME/KEY: MISC_FEATURE
<222> LOCATION: (2)..(5)
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (8)..(8)
<223> OTHER INFORMATION: Xaa = H, K ou L
<220> FEATURE:
<221> NAME/KEY: MISC_FEATURE
<222> LOCATION: (10)..(10)
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (16)..(16)
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (18)..(19)
```

```
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (24)..(24)
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (27)..(27)
<223> OTHER INFORMATION: Xaa = D or E
<220> FEATURE:
<221> NAME/KEY: MISC_FEATURE
<222> LOCATION: (30)..(31)
<223> OTHER INFORMATION: Xaa = A, V, L, I, P, W, F, M, G, S, T, Y, C, Q
      or N
<220> FEATURE:
<221> NAME/KEY: MISC_FEATURE
<222> LOCATION: (37)..(37)
<223> OTHER INFORMATION: Xaa = K, L or H
<220> FEATURE:
<221> NAME/KEY: MISC_FEATURE
<222> LOCATION: (42)..(43)
<223> OTHER INFORMATION: Xaa = A, V, L, I, P, W, F, M, G, S, T, Y, C, Q
      or N

<400> SEQUENCE: 1

Asp Xaa Xaa Xaa Xaa Lys Ser Xaa Gln Xaa Ala Trp Gly Ser Ser Xaa
1               5                   10                  15

Arg Xaa Xaa Tyr Thr Phe Ser Xaa Val Glu Xaa Phe Trp Xaa Xaa Tyr
            20                  25                  30

Asn Asn Ile His Xaa Pro Ser Lys Leu Xaa Xaa Gly Ala Asp
        35                  40                  45

<210> SEQ ID NO 2
<211> LENGTH: 961
<212> TYPE: DNA
<213> ORGANISM: Nicotiana sp.
<220> FEATURE:
<221> NAME/KEY: misc_feature
<222> LOCATION: (1)..(961)
<223> OTHER INFORMATION: cDNA of the eIF4E gene
<220> FEATURE:
<221> NAME/KEY: CDS
<222> LOCATION: (148)..(816)

<400> SEQUENCE: 2
gaattcggca cgaggaaaca ttgaactttt cctacgaata caaattcgga atttctgtga      60
gaagttacac attttcagtt gaaacccatc accaaaagtc caaatcaca aatttccaga     120 cgaaagctat gtgttgagaa caccaaa atg gtt gat gaa gta gag aaa ccg gtg    174
                              Met Val Asp Glu Val Glu Lys Pro Val
                              1               5 tcg tta gag gaa tcg aag act aat act cgt gag gtg gaa gag gaa gga    222
Ser Leu Glu Glu Ser Lys Thr Asn Thr Arg Glu Val Glu Glu Glu Gly
10              15                  20                  25 gag atc gtg ggg gaa tca gac gat acg atg tcg tct tta ggg aac cca    270
Glu Ile Val Gly Glu Ser Asp Asp Thr Met Ser Ser Leu Gly Asn Pro
            30                  35                  40 agc atg gca atg aaa cac gcg cta gaa cat tca tgg aca ttt tgg ttc    318
Ser Met Ala Met Lys His Ala Leu Glu His Ser Trp Thr Phe Trp Phe
        45                  50                  55 gat aac cca tca ggg aaa tca aaa cag gct gct tgg ggt agt tcc att    366
Asp Asn Pro Ser Gly Lys Ser Lys Gln Ala Ala Trp Gly Ser Ser Ile
    60                  65                  70 cga cca att tac acc ttc tcc act gtc gaa gat ttt tgg agt gtg tac    414
Arg Pro Ile Tyr Thr Phe Ser Thr Val Glu Asp Phe Trp Ser Val Tyr
75                  80                  85
```

```
aac aat atc cac cac cca agc aaa ttg gct gtg ggg gca gac ttt cac    462
Asn Asn Ile His His Pro Ser Lys Leu Ala Val Gly Ala Asp Phe His
 90              95                 100                 105 tgt ttt aag aat aaa att gag cca aag tgg gag gat cct gtc tgc gcc    510
Cys Phe Lys Asn Lys Ile Glu Pro Lys Trp Glu Asp Pro Val Cys Ala
                 110                 115                 120 aac gga gga aag tgg aca atg agc ttt tcg agg ggt aaa tct gat acc    558
Asn Gly Gly Lys Trp Thr Met Ser Phe Ser Arg Gly Lys Ser Asp Thr
             125                 130                 135 tgc tgg ctg tat acg ctg ctg gct atg att gga gaa caa ttt gac tgc    606
Cys Trp Leu Tyr Thr Leu Leu Ala Met Ile Gly Glu Gln Phe Asp Cys
         140                 145                 150 gga gat gaa att tgt gga gct gtt att aat gtt cga gtt aga caa gaa    654
Gly Asp Glu Ile Cys Gly Ala Val Ile Asn Val Arg Val Arg Gln Glu
 155                 160                 165 aaa ata gct ttg tgg acc agg aat gct gcc aat gaa aca gct cag gtg    702
Lys Ile Ala Leu Trp Thr Arg Asn Ala Ala Asn Glu Thr Ala Gln Val
170             175                 180                 185 agc att ggt aaa cag tgg aag gaa ttt ctg gat tac aat gac tcg gtt    750
Ser Ile Gly Lys Gln Trp Lys Glu Phe Leu Asp Tyr Asn Asp Ser Val
                 190                 195                 200 ggc ttt ata ttt cat gat gat gca aag aag cta gac aga gct gcc aag    798
Gly Phe Ile Phe His Asp Asp Ala Lys Lys Leu Asp Arg Ala Ala Lys
             205                 210                 215 aat cgt tat tct gtg tag ttctatcgtt acaataggaa ttgtgaacga           846
Asn Arg Tyr Ser Val
             220 cacagttact gagaagcagt cacctgtggc tgcctgtttt gaccgcttac attggtattc  906 acagttttca taaggaaatt tgtttggttt tgaaaaaaaa aaaaaaaaaa aaaaa       961

<210> SEQ ID NO 3
<211> LENGTH: 222
<212> TYPE: PRT
<213> ORGANISM: Nicotiana sp.

<400> SEQUENCE: 3

Met Val Asp Glu Val Glu Lys Pro Val Ser Leu Glu Glu Ser Lys Thr
 1               5                  10                  15

Asn Thr Arg Glu Val Glu Glu Glu Gly Glu Ile Val Gly Glu Ser Asp
             20                  25                  30

Asp Thr Met Ser Ser Leu Gly Asn Pro Ser Met Ala Met Lys His Ala
         35                  40                  45

Leu Glu His Ser Trp Thr Phe Trp Phe Asp Asn Pro Ser Gly Lys Ser
 50                  55                  60

Lys Gln Ala Ala Trp Gly Ser Ser Ile Arg Pro Ile Tyr Thr Phe Ser
 65                  70                  75                  80

Thr Val Glu Asp Phe Trp Ser Val Tyr Asn Asn Ile His His Pro Ser
                 85                  90                  95

Lys Leu Ala Val Gly Ala Asp Phe His Cys Phe Lys Asn Lys Ile Glu
            100                 105                 110

Pro Lys Trp Glu Asp Pro Val Cys Ala Asn Gly Gly Lys Trp Thr Met
        115                 120                 125

Ser Phe Ser Arg Gly Lys Ser Asp Thr Cys Trp Leu Tyr Thr Leu Leu
    130                 135                 140

Ala Met Ile Gly Glu Gln Phe Asp Cys Gly Asp Glu Ile Cys Gly Ala
145                 150                 155                 160

Val Ile Asn Val Arg Val Arg Gln Glu Lys Ile Ala Leu Trp Thr Arg
                165                 170                 175
```

```
Asn Ala Ala Asn Glu Thr Ala Gln Val Ser Ile Gly Lys Gln Trp Lys
            180                 185                 190

Glu Phe Leu Asp Tyr Asn Asp Ser Val Gly Phe Ile Phe His Asp Asp
        195                 200                 205

Ala Lys Lys Leu Asp Arg Ala Ala Lys Asn Arg Tyr Ser Val
    210                 215                 220

<210> SEQ ID NO 4
<211> LENGTH: 696
<212> TYPE: DNA
<213> ORGANISM: Lycopersicon esculentum
<220> FEATURE:
<221> NAME/KEY: CDS
<222> LOCATION: (1)..(696)
<223> OTHER INFORMATION: eIF4E var. Mospomorist

<400> SEQUENCE: 4
```

| | | | | | | | | | | | | | | | | |
|---|---|---|---|---|---|---|---|---|---|---|---|---|---|---|---|---|
| atg | gca | gca | gct | gaa | atg | gag | aga | acg | atg | tcg | ttt | gat | gca | gct | gag | 48 |
| Met | Ala | Ala | Ala | Glu | Met | Glu | Arg | Thr | Met | Ser | Phe | Asp | Ala | Ala | Glu | |
| 1 | | | | 5 | | | | | 10 | | | | | 15 | | |
| aag | ttg | aag | gcc | gcc | gat | gga | gga | gga | gga | gag | gta | gac | gat | gaa | ctt | 96 |
| Lys | Leu | Lys | Ala | Ala | Asp | Gly | Gly | Gly | Gly | Glu | Val | Asp | Asp | Glu | Leu | |
| | | | 20 | | | | | 25 | | | | | 30 | | | |
| gaa | gaa | ggt | gaa | att | gtt | gaa | gaa | tca | aat | gat | acg | gca | tcg | tat | tta | 144 |
| Glu | Glu | Gly | Glu | Ile | Val | Glu | Glu | Ser | Asn | Asp | Thr | Ala | Ser | Tyr | Leu | |
| | | 35 | | | | | 40 | | | | | 45 | | | | |
| ggg | aaa | gaa | atc | aca | gtg | aag | cat | cca | ttg | gag | cat | tca | tgg | act | ttt | 192 |
| Gly | Lys | Glu | Ile | Thr | Val | Lys | His | Pro | Leu | Glu | His | Ser | Trp | Thr | Phe | |
| 50 | | | | | 55 | | | | | 60 | | | | | | |
| tgg | ttt | gat | aac | cct | acc | act | aaa | tct | cga | caa | act | gct | tgg | gga | agc | 240 |
| Trp | Phe | Asp | Asn | Pro | Thr | Thr | Lys | Ser | Arg | Gln | Thr | Ala | Trp | Gly | Ser | |
| 65 | | | | | 70 | | | | | 75 | | | | | 80 | |
| tca | ctt | cga | aat | gtc | tac | act | ttc | tcc | act | gtt | gaa | gat | ttt | tgg | ggt | 288 |
| Ser | Leu | Arg | Asn | Val | Tyr | Thr | Phe | Ser | Thr | Val | Glu | Asp | Phe | Trp | Gly | |
| | | | | 85 | | | | | 90 | | | | | 95 | | |
| gct | tac | aat | aat | atc | cat | cac | cca | agc | aag | tta | att | atg | gga | gca | gac | 336 |
| Ala | Tyr | Asn | Asn | Ile | His | His | Pro | Ser | Lys | Leu | Ile | Met | Gly | Ala | Asp | |
| | | | 100 | | | | | 105 | | | | | 110 | | | |
| ttt | cat | tgt | ttt | aag | cac | aaa | att | gag | cca | aag | tgg | gaa | gat | cct | gta | 384 |
| Phe | His | Cys | Phe | Lys | His | Lys | Ile | Glu | Pro | Lys | Trp | Glu | Asp | Pro | Val | |
| | | 115 | | | | | 120 | | | | | 125 | | | | |
| tgt | gcc | aat | gga | ggg | acg | tgg | aaa | atg | agt | ttt | tcg | aag | ggt | aaa | tct | 432 |
| Cys | Ala | Asn | Gly | Gly | Thr | Trp | Lys | Met | Ser | Phe | Ser | Lys | Gly | Lys | Ser | |
| 130 | | | | | 135 | | | | | 140 | | | | | | |
| gat | acc | agc | cgg | ctg | tat | acg | ctg | ctg | gca | atg | att | gga | cat | caa | ttc | 480 |
| Asp | Thr | Ser | Arg | Leu | Tyr | Thr | Leu | Leu | Ala | Met | Ile | Gly | His | Gln | Phe | |
| 145 | | | | | 150 | | | | | 155 | | | | | 160 | |
| gat | cat | gga | gat | gaa | att | tgt | gga | gca | gtt | gtt | agt | gtc | cgg | gct | aag | 528 |
| Asp | His | Gly | Asp | Glu | Ile | Cys | Gly | Ala | Val | Val | Ser | Val | Arg | Ala | Lys | |
| | | | | 165 | | | | | 170 | | | | | 175 | | |
| gga | gaa | aaa | ata | gct | ttg | tgg | acc | aag | aat | gct | gca | aat | gaa | aca | gct | 576 |
| Gly | Glu | Lys | Ile | Ala | Leu | Trp | Thr | Lys | Asn | Ala | Ala | Asn | Glu | Thr | Ala | |
| | | | 180 | | | | | 185 | | | | | 190 | | | |
| cag | gtt | agc | att | ggt | aag | caa | tgg | aag | cag | ttt | cta | gat | tac | agt | gat | 624 |
| Gln | Val | Ser | Ile | Gly | Lys | Gln | Trp | Lys | Gln | Phe | Leu | Asp | Tyr | Ser | Asp | |
| | | 195 | | | | | 200 | | | | | 205 | | | | |
| tcg | gtt | ggc | ttc | ata | ttt | cac | gac | gat | gca | aag | agg | ctc | gac | aga | aat | 672 |
| Ser | Val | Gly | Phe | Ile | Phe | His | Asp | Asp | Ala | Lys | Arg | Leu | Asp | Arg | Asn | |
| | 210 | | | | | 215 | | | | | 220 | | | | | |
| gcc | ttg | aat | cgt | tac | acc | gta | tag | | | | | | | | | 696 |
| Ala | Leu | Asn | Arg | Tyr | Thr | Val | | | | | | | | | | |

<210> SEQ ID NO 5
<211> LENGTH: 231
<212> TYPE: PRT
<213> ORGANISM: Lycopersicon esculentum

<400> SEQUENCE: 5

Met Ala Ala Ala Glu Met Glu Arg Thr Met Ser Phe Asp Ala Ala Glu
1               5                   10                  15

Lys Leu Lys Ala Ala Asp Gly Gly Gly Glu Val Asp Asp Glu Leu
            20                  25                  30

Glu Glu Gly Glu Ile Val Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60

Trp Phe Asp Asn Pro Thr Thr Lys Ser Arg Gln Thr Ala Trp Gly Ser
65                  70                  75                  80

Ser Leu Arg Asn Val Tyr Thr Phe Ser Thr Val Glu Asp Phe Trp Gly
                85                  90                  95

Ala Tyr Asn Asn Ile His His Pro Ser Lys Leu Ile Met Gly Ala Asp
            100                 105                 110

Phe His Cys Phe Lys His Lys Ile Glu Pro Lys Trp Glu Asp Pro Val
        115                 120                 125

Cys Ala Asn Gly Gly Thr Trp Lys Met Ser Phe Ser Lys Gly Lys Ser
    130                 135                 140

Asp Thr Ser Arg Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Asn
    210                 215                 220

Ala Leu Asn Arg Tyr Thr Val
225                 230

<210> SEQ ID NO 6
<211> LENGTH: 811
<212> TYPE: DNA
<213> ORGANISM: Capsicum annuum
<220> FEATURE:
<221> NAME/KEY: misc_feature
<222> LOCATION: (1)..(811)
<223> OTHER INFORMATION: eIF4E coding sequence and 3'UTR
      Yolo Wonder genotype carrying the pvr2+ dominant allele
      for sensitivity.
<220> FEATURE:
<221> NAME/KEY: misc_feature
<222> LOCATION: (195)..(204)
<223> OTHER INFORMATION: TspRI restriction site
<220> FEATURE:
<221> NAME/KEY: CDS
<222> LOCATION: (1)..(687)
<220> FEATURE:
<221> NAME/KEY: misc_feature
<222> LOCATION: (688)..(811)
<223> OTHER INFORMATION: 3'UTR

<400> SEQUENCE: 6

```
atg gca aca gct gaa atg gag aaa acg acg acg ttt gat gaa gct gag      48
Met Ala Thr Ala Glu Met Glu Lys Thr Thr Thr Phe Asp Glu Ala Glu
1               5                   10                  15 aag gtg aaa ttg aat gct aat gag gca gat gat gaa gtt gaa gaa ggt      96
Lys Val Lys Leu Asn Ala Asn Glu Ala Asp Asp Glu Val Glu Glu Gly
            20                  25                  30 gaa att gtt gaa gaa act gat gat acg acg tcg tat ttg agc aaa gaa     144
Glu Ile Val Glu Glu Thr Asp Asp Thr Thr Ser Tyr Leu Ser Lys Glu
        35                  40                  45 ata gca aca aag cat cca tta gag cat tca tgg act ttc tgg ttt gat     192
Ile Ala Thr Lys His Pro Leu Glu His Ser Trp Thr Phe Trp Phe Asp
    50                  55                  60 aat cca gtg gcg aaa tcg aaa caa gct gct tgg ggt agc tcg ctt cgc     240
Asn Pro Val Ala Lys Ser Lys Gln Ala Ala Trp Gly Ser Ser Leu Arg
65                  70                  75                  80 aac gtc tac act ttc tcc act gtt gaa gat ttt tgg ggt gct tac aat     288
Asn Val Tyr Thr Phe Ser Thr Val Glu Asp Phe Trp Gly Ala Tyr Asn
                85                  90                  95 aat atc cac cac cca agc aag tta gtt gtg gga gca gac tta cat tgt     336
Asn Ile His His Pro Ser Lys Leu Val Val Gly Ala Asp Leu His Cys
            100                 105                 110 ttc aag cat aaa att gag cca aag tgg gaa gat cct gta tgt gcc aat     384
Phe Lys His Lys Ile Glu Pro Lys Trp Glu Asp Pro Val Cys Ala Asn
        115                 120                 125 gga ggg aca tgg aaa atg agt ttt tca aag ggt aaa tct gat acc agc     432
Gly Gly Thr Trp Lys Met Ser Phe Ser Lys Gly Lys Ser Asp Thr Ser
    130                 135                 140 tgg cta tat acg ctg ctt gca atg att gga cat caa ttc gat cat gaa     480
Trp Leu Tyr Thr Leu Leu Ala Met Ile Gly His Gln Phe Asp His Glu
145                 150                 155                 160 gat gaa att tgt gga gca gta gtt agt gtc aga ggt aag gga gaa aaa     528
Asp Glu Ile Cys Gly Ala Val Val Ser Val Arg Gly Lys Gly Glu Lys
                165                 170                 175 ata tct ttg tgg acc aag aat gct gca aat gaa acg gct cag gtt agc     576
Ile Ser Leu Trp Thr Lys Asn Ala Ala Asn Glu Thr Ala Gln Val Ser
            180                 185                 190 att ggt aag caa tgg aag cag ttt ctg gat tac agc gac agt gtt ggc     624
Ile Gly Lys Gln Trp Lys Gln Phe Leu Asp Tyr Ser Asp Ser Val Gly
        195                 200                 205 ttc ata ttt cac gac gat gca aag agg ctc gac aga aat gca aag aat     672
Phe Ile Phe His Asp Asp Ala Lys Arg Leu Asp Arg Asn Ala Lys Asn
    210                 215                 220 cgt tac aca gta taa ttcttgatgc aatgtcggaa tataagaaac acaattcgta    727
Arg Tyr Thr Val
225 ctgaaaagtt gaatcactag tgaattcgcg gccgcctgca ggtcgaccat atgggagagc    787 tcccaacgcg ttggatgcat agct                                          811
```

<210> SEQ ID NO 7
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E coding sequence and 3'UTR
      Yolo Wonder genotype carrying the pvr2+ dominant allele
      for sensitivity.
<220> FEATURE:
<221> NAME/KEY: misc_feature
<222> LOCATION: (195)..(204)
<223> OTHER INFORMATION: TspRI restriction site

<400> SEQUENCE: 7

```
Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225
```

```
<210> SEQ ID NO 8
<211> LENGTH: 811
<212> TYPE: DNA
<213> ORGANISM: Capsicum annuum
<220> FEATURE:
<221> NAME/KEY: misc_feature
<222> LOCATION: (1)..(811)
<223> OTHER INFORMATION: eIF4E coding sequence and 3'UTR
      Yolo Y genotype carrying the pvr21 allele for resistance
<220> FEATURE:
<221> NAME/KEY: CDS
<222> LOCATION: (1)..(687)
<220> FEATURE:
<221> NAME/KEY: misc_feature
<222> LOCATION: (233)..(236)
<223> OTHER INFORMATION: MvnI restriction site
<220> FEATURE:
<221> NAME/KEY: misc_feature
<222> LOCATION: (688)..(811)
<223> OTHER INFORMATION: 3'UTR
```

<400> SEQUENCE: 8

```
atg gca aca gct gaa atg gag aaa acg acg acg ttt gat gaa gct gag    48
Met Ala Thr Ala Glu Met Glu Lys Thr Thr Thr Phe Asp Glu Ala Glu
1               5                   10                  15 aag gtg aaa ttg aat gct aat gag gca gat gat gaa gtt gaa gaa ggt    96
Lys Val Lys Leu Asn Ala Asn Glu Ala Asp Asp Glu Val Glu Glu Gly
            20                  25                  30 gaa att gtt gaa gaa act gat gat acg acg tcg tat ttg agc aaa gaa   144
```

```
                ata gca aca aag cat cca tta gag cat tca tgg act ttc tgg ttt gat      192
                Ile Ala Thr Lys His Pro Leu Glu His Ser Trp Thr Phe Trp Phe Asp
                    50                  55                  60 aat cca gag gcg aaa tcg aaa caa gct gct tgg ggt agc tcg cgt cgc      240
                Asn Pro Glu Ala Lys Ser Lys Gln Ala Ala Trp Gly Ser Ser Arg Arg
                65                  70                  75                  80 aac gtc tac act ttc tcc act gtt gaa gat ttt tgg ggt gct tac aat      288
                Asn Val Tyr Thr Phe Ser Thr Val Glu Asp Phe Trp Gly Ala Tyr Asn
                                85                  90                  95 aat atc cac cac cca agc aag tta gtt gtg gga gca gac tta cat tgt      336
                Asn Ile His His Pro Ser Lys Leu Val Val Gly Ala Asp Leu His Cys
                            100                 105                 110 ttc aag cat aaa att gag cca aag tgg gaa gat cct gta tgt gcc aat      384
                Phe Lys His Lys Ile Glu Pro Lys Trp Glu Asp Pro Val Cys Ala Asn
                        115                 120                 125 gga ggg aca tgg aaa atg agt ttt tca aag ggt aaa tct gat acc agc      432
                Gly Gly Thr Trp Lys Met Ser Phe Ser Lys Gly Lys Ser Asp Thr Ser
                130                 135                 140 tgg cta tat acg ctg ctt gca atg att gga cat caa ttc gat cat gaa      480
                Trp Leu Tyr Thr Leu Leu Ala Met Ile Gly His Gln Phe Asp His Glu
                145                 150                 155                 160 gat gaa att tgt gga gca gta gtt agt gtc aga ggt aag gga gaa aaa      528
                Asp Glu Ile Cys Gly Ala Val Val Ser Val Arg Gly Lys Gly Glu Lys
                                165                 170                 175 ata tct ttg tgg acc aag aat gct gca aat gaa acg gct cag gtt agc      576
                Ile Ser Leu Trp Thr Lys Asn Ala Ala Asn Glu Thr Ala Gln Val Ser
                            180                 185                 190 att ggt aag caa tgg aag cag ttt ctg gat tac agc gac agt gtt ggc      624
                Ile Gly Lys Gln Trp Lys Gln Phe Leu Asp Tyr Ser Asp Ser Val Gly
                        195                 200                 205 ttc ata ttt cac gac gat gca aag agg ctc gac aga aat gca aag aat      672
                Phe Ile Phe His Asp Asp Ala Lys Arg Leu Asp Arg Asn Ala Lys Asn
                210                 215                 220 cgt tac aca gta taa ttcttgatgc aatgtcggaa tataagaaac acaattcgta     727
                Arg Tyr Thr Val
                225 ctgaaaagtt gaattcactag tgaattcgcg gccgcctgca ggtcgaccat atgggagagc    787 tcccaacgcg ttggatgcat agct                                           811

<210> SEQ ID NO 9
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E coding sequence and 3'UTR
      Yolo Y genotype carrying the pvr21 allele for resistance
<220> FEATURE:
<221> NAME/KEY: misc_feature
<222> LOCATION: (233)..(236)
<223> OTHER INFORMATION: MvnI restriction site

<400> SEQUENCE: 9

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45
```

```
Ile Ala Thr Lys His Pro Leu Glu His Ser Trp Thr Phe Trp Phe Asp
 50                  55                  60

Asn Pro Glu Ala Lys Ser Lys Gln Ala Ala Trp Gly Ser Ser Arg Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
130                 135                 140

Trp Leu Tyr Thr Leu Leu Ala Met Ile Gly Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
210                 215                 220

Arg Tyr Thr Val
225

<210> SEQ ID NO 10
<211> LENGTH: 32
<212> TYPE: DNA
<213> ORGANISM: Artificial Sequence
<220> FEATURE:
<223> OTHER INFORMATION: Degenerate primer

<400> SEQUENCE: 10
tctagataca ayaatatcca ycacccaagc aa                                 32

<210> SEQ ID NO 11
<211> LENGTH: 28
<212> TYPE: DNA
<213> ORGANISM: Artificial Sequence
<220> FEATURE:
<223> OTHER INFORMATION: Degenerate primer

<400> SEQUENCE: 11
tctagatggg rgcagacttt caytgttt                                      28

<210> SEQ ID NO 12
<211> LENGTH: 18
<212> TYPE: DNA
<213> ORGANISM: Capsicum annuum

<400> SEQUENCE: 12
gtatgagaaa ctaaacta                                                 18

<210> SEQ ID NO 13
<211> LENGTH: 25
<212> TYPE: DNA
<213> ORGANISM: Capsicum annuum

<400> SEQUENCE: 13 caactttca gtacgaattg tgttt                                          25
```

```
<210> SEQ ID NO 14
<211> LENGTH: 25
<212> TYPE: DNA
<213> ORGANISM: Capsicum annuum

<400> SEQUENCE: 14
tccgacattg catcaagaat tatac                                            25

<210> SEQ ID NO 15
<211> LENGTH: 18
<212> TYPE: DNA
<213> ORGANISM: Lycopersicon esculentum

<400> SEQUENCE: 15
aaatgagaaa ctaaacta                                                    18

<210> SEQ ID NO 16
<211> LENGTH: 25
<212> TYPE: DNA
<213> ORGANISM: Lycopersicon esculentum

<400> SEQUENCE: 16
ctttccagta cgaattgtgt ttctt                                            25

<210> SEQ ID NO 17
<211> LENGTH: 25
<212> TYPE: DNA
<213> ORGANISM: Lycopersicon esculentum

<400> SEQUENCE: 17
ctgcatcaag aactatacgg tgtaa                                            25

<210> SEQ ID NO 18
<211> LENGTH: 20
<212> TYPE: DNA
<213> ORGANISM: Capsicum annuum

<400> SEQUENCE: 18
aaaagcacac agcaccaaca                                                  20

<210> SEQ ID NO 19
<211> LENGTH: 22
<212> TYPE: DNA
<213> ORGANISM: Capsicum annuum

<400> SEQUENCE: 19
tattccgaca ttgcatcaag aa                                               22

<210> SEQ ID NO 20
<211> LENGTH: 24
<212> TYPE: DNA
<213> ORGANISM: Capsicum annuum

<400> SEQUENCE: 20
agactttcat tgtttcaagc ataa                                             24

<210> SEQ ID NO 21
<211> LENGTH: 25
<212> TYPE: DNA
<213> ORGANISM: Capsicum annuum

<400> SEQUENCE: 21
gattagaaag tgcaaacacc aatac                                            25
```

<210> SEQ ID NO 22
<211> LENGTH: 228
<212> TYPE: PRT
<213> ORGANISM: Capsicum annuum
<220> FEATURE:
<221> NAME/KEY: VARIANT
<222> LOCATION: (67)..(67)
<223> OTHER INFORMATION: Glu in Yolo Y, Avelar, Vania, PM994, Florida,
      C69, CM334, PM1014, and Per
<220> FEATURE:
<221> NAME/KEY: VARIANT
<222> LOCATION: (205)..(205)
<223> OTHER INFORMATION: Gly in PM1008, C69, CM334, PM1014, and Per
<220> FEATURE:
<221> NAME/KEY: VARIANT
<222> LOCATION: (109)..(109)
<223> OTHER INFORMATION: Asn in Florida
<220> FEATURE:
<221> NAME/KEY: VARIANT
<222> LOCATION: (79)..(79)
<223> OTHER INFORMATION: Arg in Yolo Y, Avelar, Vania, PM994
<220> FEATURE:
<221> NAME/KEY: VARIANT
<222> LOCATION: (68)..(68)
<223> OTHER INFORMATION: Glu chez PM 1008
<220> FEATURE:
<221> NAME/KEY: VARIANT
<222> LOCATION: (73)..(73)
<223> OTHER INFORMATION: Asp chez PM 1008
<220> FEATURE:
<221> NAME/KEY: VARIANT
<222> LOCATION: (74)..(74)
<223> OTHER INFORMATION: Asp chez PM 1008

<400> SEQUENCE: 22

```
Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220
```

<210> SEQ ID NO 23
<211> LENGTH: 231
<212> TYPE: PRT
<213> ORGANISM: Lycopersicon hirsutum
<220> FEATURE:
<221> NAME/KEY: VARIANT
<222> LOCATION: (48)..(48)
<223> OTHER INFORMATION: Phe in PI247087
<220> FEATURE:
<221> NAME/KEY: VARIANT
<222> LOCATION: (68)..(68)
<223> OTHER INFORMATION: Lys in PI247087
<220> FEATURE:
<221> NAME/KEY: VARIANT
<222> LOCATION: (77)..(77)
<223> OTHER INFORMATION: Asp chez PI247087
<220> FEATURE:
<221> NAME/KEY: VARIANT
<222> LOCATION: (109)..(109)
<223> OTHER INFORMATION: Met in PI247087

<400> SEQUENCE: 23

Met Ala Ala Ala Glu Met Glu Arg Thr Met Ser Phe Asp Ala Ala Glu
1               5                   10                  15

Lys Leu Lys Ala Ala Asp Gly Gly Gly Glu Val Asp Asp Glu Leu
            20                  25                  30

Glu Glu Gly Glu Ile Val Glu Ser Asn Asp Thr Ala Ser Tyr Leu
        35                  40                  45

Gly Lys Glu Ile Thr Val Lys His Pro Leu Glu His Ser Trp Thr Phe
    50                  55                  60

Trp Phe Asp Asn Ser Thr Thr Lys Ser Arg Gln Thr Ala Trp Gly Ser
65                  70                  75                  80

Ser Leu Arg Asn Leu Tyr Thr Phe Ser Thr Val Glu Asp Phe Trp Gly
                85                  90                  95

Ala Tyr Asn Asn Ile His His Pro Ser Lys Leu Ile Met Gly Ala Asp
            100                 105                 110

Phe His Cys Phe Lys His Lys Ile Glu Pro Gln Trp Glu Asp Pro Val
        115                 120                 125

Cys Ala Asn Gly Gly Thr Trp Lys Met Ser Phe Ser Lys Gly Lys Ser
130                 135                 140

Asp Thr Ser Trp Leu Tyr Thr Leu Leu Ala Met Ile Gly His Gln Phe
145                 150                 155                 160

Asp His Gly Asp Glu Ile Cys Gly Ala Val Val Ser Val Arg Ala Lys
                165                 170                 175

Gly Glu Lys Ile Ala Leu Trp Thr Lys Asn Ala Ala Asn Glu Thr Ala
            180                 185                 190

Gln Val Ser Ile Gly Lys Gln Trp Lys Gln Phe Leu Asp Tyr Ser Asp
        195                 200                 205

Ser Val Gly Phe Ile Phe His Asp Asp Ala Lys Arg Leu Asp Arg Ser
    210                 215                 220

Ala Leu Asn Arg Tyr Thr Val
225                 230

<210> SEQ ID NO 24
<211> LENGTH: 9
<212> TYPE: DNA
<213> ORGANISM: Artificial
<220> FEATURE:
<221> NAME/KEY: misc_feature
<222> LOCATION: (1)..(9)

-continued

```
<223> OTHER INFORMATION: synthetic

<400> SEQUENCE: 24 nncastgnn                                                              9

<210> SEQ ID NO 25
<211> LENGTH: 9
<212> TYPE: DNA
<213> ORGANISM: Artificial
<220> FEATURE:
<221> NAME/KEY: misc_feature
<222> LOCATION: (1)..(9)
<223> OTHER INFORMATION: synthetic

<400> SEQUENCE: 25 nngtsacnn                                                              9

<210> SEQ ID NO 26
<211> LENGTH: 228
<212> TYPE: PRT
<213> ORGANISM: Capsicum annuum
<220> FEATURE:
<221> NAME/KEY: misc_feature
<222> LOCATION: (67)..(67)
<223> OTHER INFORMATION: Xaa is V for variants YW, DDL, and PM1008; Xaa
      is E for variants YY, Avelar, Vania, PM994, Florida, C69, CM334,
      PM1014, and Per.
<220> FEATURE:
<221> NAME/KEY: misc_feature
<222> LOCATION: (68)..(68)
<223> OTHER INFORMATION: Xaa is A for variants YW, DDL,YY, Avelar,
      Vania, PM994, Florida, C69, CM334, PM1014, and Per. Xaa is E for
      variant PM1008.
<220> FEATURE:
<221> NAME/KEY: misc_feature
<222> LOCATION: (73)..(74)
<223> OTHER INFORMATION: Xaa-Xaa is AA for variants YW, DDL,YY, Avelar,
      Vania, PM994, Florida, C69, CM334, PM1014, and Per. Xaa-Xaa is
      DD for variant PM1008.
<220> FEATURE:
<221> NAME/KEY: misc_feature
<222> LOCATION: (79)..(79)
<223> OTHER INFORMATION: Xaa is L for variants YW, DDL, PM1008, Florida,
      C69, CM334, PM1014, and Per. Xaa is R for variants YY, Avelar,
      Vania and PM994.

<400> SEQUENCE: 26

Met Ala Thr Ala Glu Met Glu Lys Thr Thr Thr Phe Asp Glu Ala Glu
  1               5                  10                  15

Lys Val Lys Leu Asn Ala Asn Glu Ala Asp Asp Glu Val Glu Glu Gly
                 20                  25                  30

Glu Ile Val Glu Glu Thr Asp Asp Thr Thr Ser Tyr Leu Ser Lys Glu
             35                  40                  45

Ile Ala Thr Lys His Pro Leu Glu His Ser Trp Thr Phe Trp Phe Asp
 50                  55                  60

Asn Pro Xaa Xaa Lys Ser Lys Gln Xaa Xaa Trp Gly Ser Ser Xaa Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
            115                 120                 125

Gly Gly Thr Trp Lys Met Ser Phe Ser Lys Gly Lys Ser Asp Thr Ser
        130                 135                 140

Trp Leu Tyr Thr Leu Leu Ala Met Ile Gly His Gln Phe Asp His Glu
```

```
                  145                 150                 155                 160
Asp Glu Ile Cys Gly Ala Val Val Ser Val Arg Gly Lys Gly Glu Lys
                  165                 170                 175

Ile Ser Leu Trp Thr Lys Asn Ala Ala Asn Glu Thr Ala Gln Val Ser
                  180                 185                 190

Ile Gly Lys Gln Trp Lys Gln Phe Leu Asp Tyr Ser Asp Ser Val Gly
                  195                 200                 205

Phe Ile Phe His Asp Asp Ala Lys Arg Leu Asp Arg Asn Ala Lys Asn
            210                 215                 220

Arg Tyr Thr Val
225

<210> SEQ ID NO 27
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E DDL variety

<400> SEQUENCE: 27

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
                  20                  25                  30

Glu Ile Val Glu Glu Thr Asp Asp Thr Thr Ser Tyr Leu Ser Lys Glu
                  35                  40                  45

Ile Ala Thr Lys His Pro Leu Glu His Ser Trp Thr Phe Trp Phe Asp
            50                  55                  60

Asn Pro Val Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                  85                  90                  95

Asn Ile His His Pro Ser Lys Leu Val Val Gly Ala Asp Leu His Cys
                  100                 105                 110

Phe Lys His Lys Ile Glu Pro Lys Trp Glu Asp Pro Val Cys Ala Asn
            115                 120                 125

Gly Gly Thr Trp Lys Met Ser Phe Ser Lys Gly Lys Ser Asp Thr Ser
130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                  165                 170                 175

Ile Ser Leu Trp Thr Lys Asn Ala Ala Asn Glu Thr Ala Gln Val Ser
                  180                 185                 190

Ile Gly Lys Gln Trp Lys Gln Phe Leu Asp Tyr Ser Asp Ser Val Gly
                  195                 200                 205

Phe Ile Phe His Asp Asp Ala Lys Arg Leu Asp Arg Asn Ala Lys Asn
            210                 215                 220

Arg Tyr Thr Val
225

<210> SEQ ID NO 28
<211> LENGTH: 228
<212> TYPE: PRT
<213> ORGANISM: Capsicum annuum
<220> FEATURE:
```

```
<221> NAME/KEY: misc_feature
<222> LOCATION: (1)..(811)
<223> OTHER INFORMATION: eIF4E PM1008 variety

<400> SEQUENCE: 28

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Val Glu Lys Ser Lys Gln Asp Asp Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225

<210> SEQ ID NO 29
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E Avelar variety

<400> SEQUENCE: 29

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95
```

```
Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225

<210> SEQ ID NO 30
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E Vania variety

<400> SEQUENCE: 30

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
```

```
<210> SEQ ID NO 31
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E PPM994 variety

<400> SEQUENCE: 31
```

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
                20                  25                  30

Glu Ile Val Glu Glu Thr Asp Asp Thr Thr Ser Tyr Leu Ser Lys Glu
            35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
    210                 215                 220

Arg Tyr Thr Val
225

```
<210> SEQ ID NO 32
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E Florida variety

<400> SEQUENCE: 32
```

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
                20                  25                  30

-continued

```
Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
 50                  55                  60

Asn Pro Glu Ala Lys Ser Lys Gln Ala Ala Trp Gly Ser Ser Leu Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Gly Ala Asn Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
        195                 200                 205

Phe Ile Phe His Asp Asp Ala Lys Arg Leu Asp Arg Asn Ala Lys Asn
210                 215                 220

Arg Tyr Thr Val
225

<210> SEQ ID NO 33
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E C69 variety

<400> SEQUENCE: 33

Met Ala Thr Ala Glu Met Glu Lys Thr Thr Thr Phe Asp Glu Ala Glu
 1               5                  10                  15

Lys Val Lys Leu Asn Ala Asn Glu Ala Asp Asp Glu Val Glu Glu Gly
             20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
 50                  55                  60

Asn Pro Glu Ala Lys Ser Lys Gln Ala Ala Trp Gly Ser Ser Leu Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
130                 135                 140

Trp Leu Tyr Thr Leu Leu Ala Met Ile Gly His Gln Phe Asp His Glu
145                 150                 155                 160
```

```
Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225

<210> SEQ ID NO 34
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E CM334 variety

<400> SEQUENCE: 34

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225

<210> SEQ ID NO 35
<211> LENGTH: 228
<212> TYPE: PRT
<213> ORGANISM: Capsicum annuum
<220> FEATURE:
<221> NAME/KEY: misc_feature
```

-continued

```
<222> LOCATION: (1)..(811)
<223> OTHER INFORMATION: eIF4E PM1014 variety

<400> SEQUENCE: 35

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Gly Ser Val Gly
        195                 200                 205

Phe Ile Phe His Asp Asp Ala Lys Arg Leu Asp Arg Asn Ala Lys Asn
    210                 215                 220

Arg Tyr Thr Val
225

<210> SEQ ID NO 36
<211> LENGTH: 228
<212> TYPE: PRT
<213> ORGANISM: Capsicum annuum
<220> FEATURE:
<221> NAME/KEY: misc_feature
<222> LOCATION: (1)..(811)
<223> OTHER INFORMATION: eIF4E Per variety

<400> SEQUENCE: 36

Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Leu Arg
65                  70                  75                  80

Asn Val Tyr Thr Phe Ser Thr Val Glu Asp Phe Trp Gly Ala Tyr Asn
                85                  90                  95
```

```
Asn Ile His His Pro Ser Lys Leu Val Val Gly Ala Asp Leu His Cys
            100             105             110

Phe Lys His Lys Ile Glu Pro Lys Trp Glu Asp Pro Val Cys Ala Asn
        115             120             125

Gly Gly Thr Trp Lys Met Ser Phe Ser Lys Gly Lys Ser Asp Thr Ser
    130             135             140

Trp Leu Tyr Thr Leu Leu Ala Met Ile Gly His Gln Phe Asp His Glu
145             150             155             160

Asp Glu Ile Cys Gly Ala Val Val Ser Val Arg Gly Lys Gly Glu Lys
                165             170             175

Ile Ser Leu Trp Thr Lys Asn Ala Ala Asn Glu Thr Ala Gln Val Ser
            180             185             190

Ile Gly Lys Gln Trp Lys Gln Phe Leu Asp Tyr Ser Gly Ser Val Gly
        195             200             205

Phe Ile Phe His Asp Asp Ala Lys Arg Leu Asp Arg Asn Ala Lys Asn
        210             215             220

Arg Tyr Thr Val
225
```

EIF4E GENE MUTATIONS AND POTYVIRUS RESISTANCE

CROSS-REFERENCE TO RELATED APPLICATIONS

This application is a national-stage filing under 35 U.S.C. §371 of PCT/FR03/00397, filed Feb. 7, 2003. Priority is also claimed to France 02/01583, filed Feb. 8, 2002 and France 02/13678, filed Oct. 31, 2002.

BACKGROUND OF THE INVENTION

1. Field of the Invention

The present invention relates to a method for selecting or obtaining potyvirus-resistant plants. The method is particularly applicable to plants of the family of Solanaceae, Cucurbitaceae, Cruciferae and Compositae. The invention also comprises the sequences for conferring potyvirus resistance and/or for labeling the genes for resistance or for sensitivity to these potyviruses.

2. Description of the Related Art

The potyvirus group, the standard member of which is PVY, for potato virus Y, is the largest plant virus group. In fact, potyviruses are capable of infecting more than 30 plant families currently registered. This group comprises at least 180 members, which corresponds to a third of the plant viruses currently known. Potyvirus transmission is effected by aphids (for example *Myzus persicae*) via the nonpersistent mode. The symptoms caused by potyviruses are abnormalities in leaf coloration (mosaics, yellowing of veins), leaf deformities, vein necroses which can result in necrosis of the entire plant, and considerable decreases in size of the sick plant, greatly influencing productivity.

The Solanaceae, Cucurbitaceae, Cruciferae and Compositae are particularly sensitive to potyviruses. The Solanaceae, and more particularly the tomato and the *capsicum* (or pepper), are infected with at least seven different potyviruses throughout the world: potato virus Y (PVY) is present on all the growing areas, whereas the others are confined to a continent (tobacco etch virus, pepper mottle virus and Peru tomato virus on the American continent, pepper veinal mottle virus and potyvirus E in Africa, and chili veinal mottle virus in Asia). This compartmentalization is, however, no longer absolute, several potyviruses having been identified outside their area of origin. In France, and more particularly in the Mediterranean basin, the predominant potyvirus is PVY. Having appeared in the 1970s, PVY epidemics developed in crops in the open field and then in crops under cover, where, from 1982, new PVY isolates were demonstrated, which caused particularly serious symptoms of necrosis in the tomato (Gëbre-Selassie et al., 1987). For some of these potyviruses, it is possible to classify the isolates according to their ability to circumvent resistance alleles. This is the case of PVY with respect to the pvr2 gene in the *capsicum*, the only resistance gene that has been used for a long time by selectors, but that is circumvented in the Mediterranean region and in tropical regions. Despite the predominance of PVY in France, the internationalization of the seed market makes it necessary for selectors who sell their seeds abroad to use genes controlling resistance to these various potyviruses. More generally, considering the economical importance of potyvirus infections and the lack of direct means for combating this type of infection, the search for resistant plant varieties constitutes one of the main lines of plant improvement.

Potyviruses have a nonenveloped filamentous structure (Langenberg and Zhang, 1997), from 680 to 900 nm long and from 11 to 15 nm wide (Dougherty and Carrington, 1988; Riechmann et al., 1992). The viral genome consists of a single-stranded sense RNA approximately 10 kb in length. The single-stranded RNA has a poly A tail at its 3' end and binds, in the 5' position to a viral protein called VPg (Murphy et al., 1990, Takahashi et al., 1997). The viral RNA encodes 10 proteins involved in polyproteins cleavage, genome replication, cell-to-cell movement and long-distance movement, transmission via aphids, etc. Virus control can only be carried out indirectly. Specifically, it is only possible to eliminate the vector of the disease (the aphids in this case) or to grow varieties resistant to the viral infection and/or to the vectors.

Faced with an attack from a pathogen (viruses, bacteria, fungi or nematodes), the plant has several strategies for defending itself or withstanding infection. Among the defense strategies, the plant can set up:

systems of mechanical defense by developing and reinforcing physical barriers consisting of a thick cuticle on the leaves and/or a deposit of callose or of lignins on the cell walls. Thus, the entry of pathogens into and their movement in the plant are made more difficult;

systems of chemical or biochemical defense by synthesizing toxic compounds such as, for example, tannins, phytoalexins and various protein complexes.

Among the resistance strategies, non-host resistance (when all the entities of a species are resistant to a given pathogen) is distinguished from host resistance (when at least one entity of the species is sensitive to a strain of the pathogenic agent). Host resistance, the most well-known and the most well-characterized to date, is that which involves a major, dominant gene. When the major gene is in the presence of a gene specific for avirulence of the pathogenic agent, the incompatibility between the plant and the pathogen is set up and the plant is resistant. This interaction, described by Flor (1955), is also called "gene-to-gene" model and is very often associated with localized necrosis of the plant tissue at the site of infection (hypersensitivity reaction). Although quite widespread, this "gene-to-gene" model is not universal because some systems of resistance described do not function according to this model, the differences lying in particular in the mode of action of the resistance gene. Genes exist which are recessive, which are superdominant or which exert incomplete dominance. Several avirulence genes can interact with the same resistance gene. Many resistances are also polygenic, several genes present in the plant are then involved in the resistance, each of them having a partially protective effect and being able to control different mechanisms.

To date, many dominant genes according to the "gene-to-gene" model have been cloned. They have related gene structures, although they act against varied pathogenic agents (viruses, fungi, bacteria, insects, nematodes). The presence of conserved domains has made it possible to define 4 major classes (Hammond-Kosack and Jones, 1997) of dominant genes.

Singularly, it is estimated that 40% of potyvirus resistances are recessive, whereas, in the other viral groups, this proportion only reaches 20% on average. Fraser (1992) has put forward the hypothesis that recessive resistances are different from dominant resistances of "gene-to-gene" type and are the result of a specific deficiency or alteration in the product of a host's gene, necessary for accomplishing the viral cycle in the plant. The dominant alleles for sensitivity are therefore thought to correspond to the availability of this product involved in the plant/pathogen interactions.

It has been shown that point mutations in the viral gene encoding the VPg protein are involved in the circumventing of potyvirus resistance in several host-pathogen couples. This has been shown in the TVMV/*Nicotiana tabacum* (va gene), PVY/tomato (pot-1 gene), LMV/lettuce (mol gene) and PSbMV/pea (sbm1 gene) couples (Keller et al., 1998, Morel, 2001, Redondo, 2001 Nicholas et al., 1997). This does not exclude the fact that other viral genes may also be involved.

Moreover, Wittman et al. (1997) have shown that an isoform of eukaryotic translation initiation factor eIF4E from *Arabidopsis thaliana* interacts with the viral protein VPg of the turnip mosaic virus (TuMV). This same interaction has been detected between TEV VPg and eIF4E from tobacco and from tomato (Schaad et al., 2000).

The eIF4E gene encodes a eukaryotic RNA translation initiation factor. eIF4E corresponds to one of the subunits of the translation factor eIF4F (in wheatgerm, it corresponds to the p26 subunit). The eIF4E translation factor binds to the mRNA cap at the $m^7Gs$. The structure of eIF4E is characterized by a region rich in tryptophan residues (10 in *Arabidopsis thaliana*, 11 in wheat and 12 in mammals). These tryptophan residues are thought to be involved in binding to the $m^7G$ functional group (Rudd, K. et al. 1998). The eIF4E translation factor is encoded by a multigene family. For example, in *Arabidopsis thaliana*, 4 copies of eIF4E have been identified (Rodriguez et al., 1998, Robaglia et al., personal communication). These copies exhibit, in pairs, between 44 and 82% identity.

All these studies make reference to the correlation between the eIF4E/VPg interaction and the sensitivity of the plant to potyviruses, but none emphasize, or even suggest, that this interaction could result in resistance. On the contrary, it is even indicated in Schaad et al., 2000, that the VPg/eIF4E interaction does not play a role in resistance since the genetic determinants of the VPa/eIF4E interaction are different from those which allow potyviruses (via VPg) to circumvent the resistance.

It is therefore to the inventors' credit, in such a state of the art, to have demonstrated eIF4E proteins, and also the corresponding genes, involved in plant resistance or sensitivity to potyviruses.

The inventors have in particular noted that various potyvirus-resistant plants have point mutations located in the same region of the eIF4E protein; this region, which is very conserved between the eIF4E proteins derived from various plant species, in particular from Solanaceae, is derined by the gene sequence (I) (SEQ ID NO: 1) below:

$DX_1X_2X_3X_4KSX_5QX_6AWGSSX_7RX_8X_9YTFSX_{10}VEX_{11}FWX_{12}X_{13}YNNIHX_{14}PSKLX_{15}X_{16}GAD$ in which:
$X_1, X_2, X_3, X_4, X_6, X_7, X_8, X_9, X_{10}, X_{12}, X_{13}, X_{15}$ and $X_{16}$ each represent a neutral amino acid;
$X_5$ and $X_{14}$ represent a basic amino acid;
$X_{11}$ represents an acidic amino acid;
D, K, S, Q, A, W, G, R, Y, T, F, V, E, N, I, H, P and L have their usual 1-letter code meaning.

The term "neutral amino acid" is here defined as any amino acid chosen from the following: alanine, valine, leucine, isoleucine, proline, tryptophan, phenylalanine, methionine, glycine, serine, threonine, tyrosine, cysteine, glutamine, asparagine. The term "charged amino acid" is defined as any amino acid chosen from the following: histidine, lysine, arginine, glutamate and aspartate. Among these charged amino acids, histidine, lysine and arginine are basic amino acids and glutamate and aspartate are acidic amino acids.

The sequence (I) is also represented in the sequence listing in the appendix under the number SEQ ID NO: 1.

The mutations demonstrated by the inventors in the pepper are as follows:
substitution of the neutral amino acid $X_3$ of sequence (I) with a basic amino acid;
substitution of the neutral amino acid $X_7$ of sequence (I) with a basic amino acid;
substitution of the aspartate residue in the C-terminal position of sequence (I) with a neutral amino acid.

The mutation of $X_3$ was observed in pepper lines exhibiting two different types of potyvirus resistance ($pvr2^1$ and $pvr2^2$); the peppers exhibiting the $pvr2^1$ phenotype also having the mutation at position $X_7$, and the peppers exhibiting the $pvr2^2$ phenotype also having the mutation in the C-terminal position.

In the tomato, the inventors have in particular observed the following mutations:
substitution of the neutral amino acid $X_1$ of sequence (I) with a basic amino acid;
substitution of the Ala residue of the AWGSS unit of sequence (I) with an acidic amino acid.

Due to the very high degree of sequence conservation of the eIF4E genes in eukaryotes and to the availability of 3D structure for the mouse and yeast eIF4E proteins (Marcotrigiano et al., 1997, Cell 89: 951-961; Matsuo et al., 1997, Nat. Struct. Biol. 4: 717-724), the positions of the mutations with respect to the 3D structure of eIF4E in the *capsicum* and the tomato can be determined. All these mutations are physically close and at the surface of the protein. Moreover, these mutations do not involve amino acids that are very conserved in eukaryotes, nor those involved in the essential functions of eIF4E, namely cap recognition or interaction between eIF4E and eIF4G or the 4E-binding protein.

However, it is probable that these mutations exert an effect on the VPg/eIF4E interaction by modification of the structure of eIF4E in the region(s) thereof involved in this interaction. This structural modification probably results from the substitution of amino acids with amino acids having a different charge (replacement of neutral amino acids with charged amino acids, or, conversely, of charged amino acids with neutral amino acids, or amino acids having an opposite charge), which constitutes the point common to all the mutations demonstrated by the inventors. It can therefore reasonably be assumed that other mutations of the same type in a plant eIF4E protein, in the region defined by sequence (I), will lead to similar structural modifications, producing the same effect on the VPa/eIF4E interaction.

In particular, it appears that the substitution of at least one of the neutral amino acids, $X_1, X_2, X_3$ or $X_4$ with a charged amino acid, in particular with a basic amino acid, plays an important role in potyvirus resistance.

These observations makes it possible to propose tools, in particular genetic tools, for screening and/or for obtaining plants resistant or sensitive to potyviruses.

The present invention relates more particularly to a method for selecting potyvirus-resistant plants, characterized in that it comprises the detection, in the plants to be tested:
of the presence or of the absence of an eIF4E protein (hereinafter called: "wild-type eIF4E protein") comprising a region defined by sequence (I) above, or of a sequence encoding said protein;
of the presence or of the absence of a mutant eIF4E protein comprising a region derived from that defined by sequence (I) above, by substitution of at least one neutral amino acid of said sequence (I) with a charged amino acid, preferably a basic amino acid, and/or substitution of at least one charged amino acid of said sequence (I) with a neutral amino acid or an amino acid having an opposite charge, or of a sequence encoding said protein;
and the selection of the plants in which a mutant eIF4E protein or a sequence encoding said protein is detected, and in which no wild-type eIF4E protein or sequence encoding said protein is detected.

A subject of the present invention is also a method for selecting plants which can be used for obtaining potyvirus-resistant plants, characterized in that it comprises the detection, in the plants to be tested, of the presence or of the absence of the mutant eIF4E protein as defined above or of a sequence encoding said protein, and the selection of the plants in which said mutant eIF4E protein or a sequence encoding said protein is detected.

According to a preferred embodiment of the invention, said mutant eIF4E protein comprises a region derived from that defined by sequence (I) above, by:
a) substitution of at least one of the amino acids $X_1$, $X_2$, $X_3$ or $X_4$ of said sequence (I) with a charged amino acid, and
b) substitution of at least one of the other neutral amino acids of said sequence (I) with a charged amino acid and/or substitution of at least one charged amino acid of said sequence (I) with a neutral amino acid or an amino acid having an opposite charge.

The detection of the presence or of the absence of a wild-type or mutant eIF4E protein can be carried out in particular using antibodies specifically directed against the desired form of the eIF4E protein. They may in particular be antibodies directed either against the wild-type form or against the mutant form of the region of eIF4E defined by sequence (I).

For the detection of the presence or of the absence of a sequence encoding a wild-type eIF4E protein or of a sequence encoding a mutant eIF4E protein, many tools are available; they may in particular be polynucleotides derived from the sequence of the eIF4E gene, and in particular polynucleotides capable of hybridizing selectively either with a wild-type allele or with a mutant allele of eIF4E, as defined above, or polynucleotides which make it possible to amplify the region of eIF4E containing the desired mutation; they may also be restriction enzymes which recognize a target sequence present in the wild-type form but not in the mutated form (or vice versa).

A subject of the present invention is thus the use of a selection tool chosen from:
a) a polynucleotide encoding a wild-type or mutant eIF4E protein as defined above;
b) a polynucleotide complementary to the polynucleotide a);
c) an fragment of at least 10 bp of a polynucleotide a) or b);
d) an antibody directed against a wild-type or mutant eIF4E protein as defined above;
for selecting potyvirus-resistant plants.

In particular, the invention relates to a method for selecting potyvirus-resistant plants, characterized in that it comprises the use of at least one means of selection chosen from the group of genetic tools (or similar) comprising:
*A/ all or part of one at least of the sequences selected from the subgroup comprising:
  SEQ ID NO: 2
  SEQ ID NO: 4
  SEQ ID NOs: 6 and 8,
  any analog of these sequences resulting from the degeneracy of the genetic code,
  any cDNA sequence complementary to at least one of these sequences and/or to at least one of their analogs;
*B/ all or part of one at least of the products of transcription of the sequences A;
*C/ all or part of one at least of the products of translation of the sequences A;
*D/ all or part of at least one antibody specific for at least one product of translation of C/;
*E/ and any combination of tools A, B, C and D.

Preferably, the means of selection are selected from the tool subgroups A/ and/or B/, and even more preferably from the tool subgroup A/.

By means of this simple, easy and reliable pinpointing of plants resistant or sensitive to potyviruses, the inventors have thus developed a new method based on the use of sequences corresponding to the eIF4E gene.

The method which is the subject of the invention applies particularly to the Solanaceae, Cucurbitaceae, Cruciferae and Compositae, and more particularly to plants of the genera *Lycopersicon, Capsicum, Nicotiana, Solanum, Lactuca, Cucumis, Arabidopsis*, etc.

The potyviruses concerned are, for example, potato virus Y (PVY), tobacco etch virus (TEV) and/or lettuce mosaic virus (LMV) and/or zucchini yellow mosaic virus (ZYMV) and/or turnip mosaic virus (TuMV).

To implement the method according to the invention, use is made of nucleotide sequences and/or peptide sequences or restriction enzymes as means of detection, probes or primers, for selecting plants resistant or sensitive to potyviruses.

These means of detection comprise in particular nucleotide probes or primers.

For the purpose of the present invention, the term "primer" is intended to mean any polynucleotide sequence which can be used for amplifying a sequence of an eIF4E gene liable to comprise a mutation associated with potyvirus resistance. They are in particular polynucleotides which can be used for amplifying all or part of the sequence of eIF4E encoding the region of eIF4E defined by sequence (I), or of the mutant sequence which is derived therefrom.

For the purpose of the present invention, the term "probe" is intended to mean any polynucleotide sequence which hybridizes with a wild-type eIF4E gene or with a mutant eIF4E gene as defined above. This includes in particular the nucleotide sequences capable of hybridizing selectively either with an allele of the eIF4E gene associated with potyvirus resistance, or with an allele of the eIF4E gene associated with potyvirus sensitivity.

These probes and these primers can be used as markers specific for the plants resistant or sensitive to potyviruses.

In accordance with the invention, it is possible to sort the potyvirus-sensitive plants from the potyvirus-resistant plants by means of the genetic tools (or similar) (A) to (E), or even specific restriction enzymes. The latter will be described below.

The nucleotide sequences (A) SEQ ID NOs: 2, 4, 6 and 8 correspond to different Solanaceae eIF4E genes involved in potyvirus resistance encoding a eukaryotic RNA translation initiation factor. SEQ ID NO: 8 corresponds to a recessive eIF4E allele for resistance to a potyvirus, while SEQ ID NOs: 2, 4, and 6 represent dominant eIF4E alleles for sensitivity to a potyvirus.

Means of selection or genetic markers for resistance or for sensitivity to potyviruses have therefore been discovered in accordance with the invention. The method of selection according to the invention can involve, separately or together, the two types of means of selection or markers.

Naturally, the invention also encompasses all the equivalents to these nucleotide sequences (A) SEQ ID NOs: 2, 4, 6 and 8, which conserve the function of eIF4E genetic marker for sensitivity/resistance to potyviruses specific to the reference sequences. As regards the DNAs, they are in particular the genetic degeneracy analogs and the cDNA sequences complementary to the reference sequences. The polynucleotide equivalents of the reference sequences (A) are also found among their transcription products (RNA) (B). The proteins (C) derived from (A) and from (B) constitute other intracellular markers for selecting plants resistant or sensitive to potyviruses. Besides the targets (A), (B) and (C), the means of selection of the invention can also be nucleotide probes capable of hybridizing with complementary nucleotide targets (A) and (B), or else protein-based means of detection (antibodies D) capable of pairing with specific antigenic targets (C). It is possible to envision combining all these equivalent means (A), (B), (C) & (D) so as to form a selection tool (E).

The means according to the invention also cover any fragment of these sequences (A), (B), (C) & (D). According to the invention, the term "fragment" is intended to mean:
- either a polynucleotide of at least 10, 20, 30, 50, 100, 200, 300, 400, 500 contiguous nucleotides of the reference sequence; preferred fragments are those which are capable of hybridizing selectively, under stringent conditions, with said reference sequence;
- or a polyamino acid of at least 3, 6, 10, 15, 30, 60, 100, 150, 200 contiguous amino acids of the reference sequence; preferred fragments are those which are capable of hybridizing selectively, under stringent conditions, with said reference sequence.

According to an advantageous embodiment of the invention, the method is characterized in that:
- at least one means of detection comprising at least one of the tools A, B, C, D, E as claimed in claim 1 and/or at least one restriction enzyme is brought into contact with at least one genomic and/or protein extract of a plant to be tested,
- said genomic and/or protein extract, optionally paired and/or hybridized and/or digested, is subjected to at least one separation,
- the possible pairings and/or hybridizations and/or digestions liable to occur are revealed,
- and the results are read so as to finally reach a conclusion as to the presence or the absence of an allele for resistance (pvr2$^1$) or of an allele for sensitivity (pvr$^+$) to at least one potyvirus.

This method falls within the framework of the methodologies known in the field of the detection and recognition of plant genetic characteristics.

According to a first embodiment of the method, in which the principle of selection is based on the use of one or more specific restriction enzymes, the method can correspond to the following methodology:
- the coding sequence of the eIF4E gene is amplified by PCR from the DNA of the plant to be tested, for example using the primers SEQ ID NOs: 18 and/or 19,
- the amplification product is digested with a suitable restriction enzyme,
- the possible fragments obtained are separated,
- and the resistant or sensitive plants are selected according to the restriction profile for said amplification product.

For example, potyvirus-sensitive plants can be detected by means of a restriction profile which reveals the presence of a site for cleavage by the TspRI enzyme or one of its isoschizomers, and potyvirus-resistant plants can be detected by means of a restriction profile which reveals the absence of said site for cleavage with TspRI or one of its isoschizomers and the presence of a site for cleavage with the MvnI enzyme or one of its isoschizomers.

According to a second embodiment of the method, corresponding to the case where the mode of selection is the hybridization of complementary nucleotide sequences, the method preferably consists:
- in extracting the DNA from plants,
- in optionally subjecting this DNA to enzymatic digestion using at least one restriction enzyme,
- in denaturing the optionally digested DNA,
- in bringing the DNA thus denatured into contact with a probe, itself denatured beforehand and provided with at least one label, so as to carry out the hybridization,
- in eliminating the DNA and the nonhybridized probe,
- in revealing the hybridization by means of the label,
- and in selecting plants which have a hybridization profile corresponding to cosegregation of the target hybridized with the labeled probe and of the allele for resistance or for sensitivity.

When the DNA has been digested with a restriction enzyme, the distinction between the sensitive plants and the resistant plants can be made by means of the difference in size of the hybridized fragments.

It can also be made using a probe capable of hybridizing selectively with the allele for resistance or the allele for sensitivity. The hybridization of the single-stranded molecules of the probe and of the target is preferably carried out under stringent hybridization conditions allowing selective hybridization, which can be determined in a manner known to those skilled in the art. In general, the hybridization and washing temperature is at least 5° C. below the Tm of the reference sequence at a given pH and for a given ionic strength. Typically, the hybridization temperature is at least 30° C. for a polynucleotide of 15 to 50 nucleotides and at least 60° C. for a polynucleotide of more than 50 nucleotides.

The level of signal generated by the interaction between the sequence capable of hybridizing selectively and the reference sequences is generally 10 times, preferably 100 times, more intense than that of the interaction of the other DNA sequences generating the background noise.

With a probe labeled, for example, with a radioactive element, such as $^{32}$P, or with a grafted enzyme, such as peroxidase, the hybridization is readily revealed qualitatively and quantitatively.

The DNA used in the first or the second embodiment can be either total DNA or cDNA.

According to a third embodiment (among others) of the method according to the invention, corresponding to the case where the mode of selection is antibody/antigen pairing, the method preferably consists in detecting the presence of a polypeptide partly consisting of all or part of one of the amino acid sequences described below and included in the invention. The method may consist in bringing the sample to be tested into contact with an antibody as described above, and then in detecting the antigen/antibody complex formed.

Whatever the mode of selection, the method of selection according to the invention is reliable and sensitive.

A subject of the present invention is also a polynucleotide encoding a mutant eIF4E protein comprising a region derived from that defined by sequence (I) above, by substitution of at least one neutral amino acid of said sequence (I) with a charged amino acid, preferably a basic amino acid, and/or substitution of at least one charged amino acid of said sequence (I) with a neutral amino acid or an amino acid having an opposite charge.

According to a preferred embodiment, said polynucleotide encodes a mutant eIF4E protein which comprises a region derived from that defined by sequence (I) above, by:
a) substitution of at least one of the amino acids $X_1$, $X_2$, $X_3$ or $X_4$ of said sequence (I) with a charged amino acid, and
b) substitution of at least one of the other neutral amino acids of said sequence (I) with a charged amino acid and/or substitution of at least one charged amino acid of said sequence (I) with a neutral amino acid or an amino acid having an opposite charge.

Polynucleotides in accordance with the invention are, for example, those which encode the variants of the sequences SEQ ID NO: 22 or 23 associated with potyvirus resistance.

According to another of its aspects, the invention concerns a nucleotide sequence characterized in that it is described by a sequence chosen from the group comprising all or some of the following sequences:
SEQ ID NO: 2
SEQ ID NO: 4
SEQ ID NO: 6
SEQ ID NO: 8.

The nucleotide sequence SEQ ID NO: 2 is a cDNA sequence obtained from tobacco DNA and corresponding to the tobacco gene. The nucleotide sequence SEQ ID NO: 4 is a sequence encoding an eIF4E protein of a potyvirus-sensitive variety of *Lycopersicon esculentum*. The sequences SEQ ID NOs: 6 and 8 are sequences encoding eIF4E proteins from *capsicum* (*Capsicum annuum*), varieties Yolo Wonder and Yolo Y, respectively.

A subject of the present invention is also primers for amplifying an eIF4E gene, or a portion thereof, liable to contain at least one mutation, as defined above, associated with potyvirus resistance; they are in particular primers for amplifying the sequence of eIF4E encoding the region of eIF4E defined by sequence (I), or a mutant sequence which is derived therefrom.

Primers in accordance with the invention can be readily defined by those skilled in the art, from the nucleotide or peptide sequences described in the present invention.

By way of nonlimiting examples, mention will be made of: the amplification primers consisting of the nucleotide primer sequences SEQ ID NOs: 18 & 19; the cloning primers SEQ ID NOs: 10 to 17; the primers for screening a BAC library, consisting of the nucleotide sequences SEQ ID NOs: 20 & 21.

SEQ ID NOs: 18 & 19 are primers derived from the coding sequence of *capsicum* Yolo Wonder eIF4E, which make it possible, in particular by PCR amplification and then by enzyme digestion, to detect the nucleotide sequences carrying the alleles for resistance, pvr2, and for sensitivity, pvr$^+$, to potyviruses. The degenerate cloning primers SEQ ID NOs: 10 & 11 and the nondegenerate cloning primers SEQ ID NOs: 12 to 17 were defined on the basis of an alignment of the eIF4E sequences from tobacco, tomato and *Arabidopsis* and used for the synthesis (RACE) of cDNA probes for detecting eIF4E in the tomato and *capsicum* genome. The primers SEQ ID NOs: 20 & 21 for screening a BAC library are nondegenerate. These primers SEQ ID NOs: 10 to 17, 20 & 21 can optionally be used directly or indirectly (construction of selection tools) in the detection of potyvirus resistance or potyvirus sensitivity characteristics.

A subject of the present invention is also a mutant eIF4E protein comprising a region derived from that defined by sequence (I) above, by substitution of at least one neutral amino acid of said sequence (I) with a charged amino acid, preferably a basic amino acid, and/or substitution of at least one charged amino acid of said sequence (I) with a neutral amino acid or an amino acid having an opposite charge.

According to a preferred embodiment, said mutant eIF4E protein comprises a region derived from that defined by sequence (I) above, by:
a) substitution of at least one of the amino acids $X_1$, $X_2$, $X_3$ or $X_4$ of said sequence (I) with a charged amino acid, and
b) substitution of at least one of the other neutral amino acids of said sequence (I) with a charged amino acid and/or substitution of at least one charged amino acid of said sequence (I) with a neutral amino acid or an amino acid having an opposite charge.

The present invention also covers the products of translation of the nucleotide sequences SEQ ID NOs: 2, 4, 6 and 8, namely the polypeptides chosen from the group comprising all or some of the following sequences:
SEQ ID NO: 3
SEQ ID NO: 5
SEQ ID NO: 7
SEQ ID NO: 9.

The means for selecting potyvirus-resistance/sensitivity of plants, consisting of amino acid sequences, are preferably used as locating targets. They are then indirect selection means which underlie the use of specific means for detecting these peptide targets.

These means of detection are advantageously antibodies which constitute another subject of the present invention. Thus, said antibodies are characterized in that they are specifically directed against all or part of one at least of the translation products C, and more particularly of the amino acid sequences SEQ ID NOs: 3, 5, 7, 9, 22 or 23 or a fragment of at least 6 amino acids thereof. These antibodies may be monoclonal or polyclonal.

The antibodies against the polypeptides as defined above can be prepared according to conventional techniques well known to those skilled in the art (for example, Kohler and Milstein, 1975; Kozbor et al. 1983, Martineau et al., 1998). An antibody according to the invention may comprise a detectable isotope or nonisotope, for example fluorescent, label or else may be coupled to a molecule such as biotin according to techniques well known to those skilled in the art.

Another section of the invention relates to means of selection made up of probes for detecting plants resistant to at least one potyvirus, these probes being taken in themselves. In this section, probes for detecting plants resistant to at least one potyvirus are defined.

A first category of probes is characterized in that each probe comprises at least one sequence corresponding to all or part of SEQ ID NOs: 2, 4, 6 and 8. Within this first category, the probes comprising at least one sequence corresponding to all or part of SEQ ID NOs: 2, 4, 6 and 8, and in particular to all or part of the portion encoding the region of the eIF4E protein defined by general sequence (I), are most especially preferred.

SEQ ID NO: 6 is a sensitivity probe derived from the *capsicum* Yolo Wonder. It differs from SEQ ID NO: 8, which is a resistance probe derived from the *capsicum* Yolo Y, by virtue of two nucleotide bases. These mutations shown on SEQ ID NOs: 6 & 8 correspond to the restriction sites TspRI for SEQ ID NO: 6 and MnvI for SEQ ID NO: 8, marking, respectively, potyvirus sensitivity in Yolo Wonder and potyvirus resistance in Yolo Y.

These probes are used to distinguish resistant and sensitive plants, either by selective hybridization and detection of the presence or of the absence of a hybridization signal, or by digestion with an appropriate restriction enzyme capable of differentially cleaving the allele for sensitivity and the allele for resistance, for example EcoRI, TspRI or MnvI, followed by hybridization of the probe with the restriction product. In the latter case, the sensitive plants are distinguished from the resistant plants by the difference in size of the hybridized fragments.

The present invention also provides tools for carrying out another method of selection in accordance with the first embodiment of the method according to the invention, as defined above. According to this first embodiment, a PCR amplification of the eIF4E sequence is first of all carried out. The amplification is followed by selective digestion with a restriction enzyme. The tools involved are therefore of two types: restriction enzyme(s) and PCR primer(s) for amplifying the eIF4E sequence.

A subject of the present invention is in particular a kit for detecting an eIF4E allele associated with potyvirus resistance or with potyvirus sensitivity, characterized in that it comprises:

at least one restriction enzyme chosen from:
a) an enzyme which recognizes a restriction site I present in at least one eIF4E allele associated with potyvirus sensitivity, and absent from the eIF4E alleles associated with potyvirus resistance;
b) an enzyme which recognizes a restriction site II present in at least one eIF4E allele associated with potyvirus resistance, and absent from the eIF4E alleles associated with potyvirus sensitivity; and a pair of nucleotide primers for amplifying eIF4E or a portion thereof comprising the restriction site I and/or the restriction site II.

For example,
for detecting an eIF4E allele associated with potyvirus sensitivity, such as that represented by the sequence SEQ ID NO: 6, the restriction enzyme is TspRI, or one of its isoschizomers, which recognizes a restriction site defined by the sense sequence: NNCASTGNN^ (SEQ ID NO: 24) and the antisense sequence ^NNGTSACNN (SEQ ID NO: 25). The nucleotide primers are chosen so as to allow amplification of the entire sequence of eIF4E or of at last one portion thereof comprising the TspRI site;

for detecting an eIF4E allele associated with potyvirus resistance, such as that represented by the sequence SEQ ID NO: 8, the restriction enzyme is MvnI, or one of its isoschizomers, which recognizes a restriction site defined by the sense sequence: CG^CG and the antisense sequence: GC^GC. The nucleotide primers are chosen so as to allow amplification of the entire sequence of eIF4E or of at least one portion thereof comprising the MvnI site.

In the two cases, the primers SEQ ID NO: 18 and SEQ ID NO: 19 may, for example, be used.

As indicated above, the detection of plants sensitive or resistant to potyviruses can also be carried out by detection of the presence or of the absence of the wild-type or mutant form of the eIF4E protein.

Thus, the present invention encompasses the use of a wild-type or mutant eIF4E protein, as defined above, or of an antibody specific for one of said proteins, for selecting potyvirus-resistant plants.

Preferably, said eIF4E protein is chosen from:
the protein represented by the polypeptide sequence SEQ ID NO: 3;
the protein represented by the polypeptide sequence SEQ ID NO: 5;
the protein represented by the polypeptide sequence SEQ ID NO: 7;
the protein represented by the polypeptide sequence SEQ ID NO: 9;
the group of proteins represented by the polypeptide sequence SEQ ID NO: 22;
the group of proteins represented by the polypeptide sequence SEQ ID NO: 23.

Thus, a category of means for detecting potyvirus resistance in accordance with the invention is characterized in that each of these means comprises at least one antibody specific for all or part of a mutant eIF4E protein in accordance with the invention, and in particular for a fragment of at least 6 amino acids thereof carrying a mutation associated with the resistance, as defined above.

For example, a means for detecting the resistance may consist of an antibody specific for all or part of a polypeptide sequence as defined above, in particular for a fragment of at least 6 amino acids thereof carrying a mutation associated with the resistance.

The invention also relates to means for detecting potyvirus sensitivity or potyvirus resistance, each consisting of at least one amino acid sequence chosen from the group comprising the following sequences:
SEQ ID NO: 3;
SEQ ID NO: 5;
SEQ ID NO: 7;
SEQ ID NO: 9;
SEQ ID NO: 22;
SEQ ID NO: 23.

The invention relates more particularly to means for detecting potyvirus sensitivity, each consisting of at least one antibody specific for an amino acid sequence chosen from the group comprising the following sequences:
SEQ ID NO: 3;
SEQ ID NO: 5;
SEQ ID NO: 7;
SEQ ID NO: 9;
SEQ ID NO: 22;
SEQ ID NO: 23;
or a fragment of at least 6 amino acids of one of said sequences, in particular a fragment of the region thereof defined by sequence (I).

Preferably, each nucleotide probe or any other means of detection mentioned above has at least one label, that is useful as an indicator of the nucleotide hybridization or the antigen/antibody pairing at the heart of the detection of the sensitive sequence. Advantageously, this label is detectable by spectroscopic, photochemical, biochemical, immunochemical or else chemical means. For example, such a label may consist of a radioactive isotope of $^{32}P$ or $^{3}H$, of a fluorescent molecule (5-bromodeoxyuridine, fluoresceine, acetylaminofluorene) or else of a ligand such as biotin. As regards more especially the nucleotide probes, the labeling thereof is preferably carried out by incorporation of labeled molecules into the polynucleotides by primer extension or else by addition to the 3' or 5' ends.

Preferably, the sequences used for detecting the potyvirus-resistant plants are used as nucleotide probes or primers.

It goes without saying that not all the abovementioned means of detection are limited strictly to the denoted sequences, but encompass all the equivalents consisting in particular of the similar sequences which conserve the function under consideration, and as defined above.

Those skilled in the art are fully aware of the various methods for preparing probes and primers, including by cloning and by the action of restriction enzymes, or else by direct chemical synthesis according to techniques such as the phosphodiester method of Brown et al. (1979) or the solid-support technique described in European patent No. EP 0707592. The nucleic acids can be labeled, if desired, by incorporating a detectable molecule or label as set out above. Examples of nonradioactive labeling of nucleic acid fragments are described in particular in French patent No. FR 78 10 975 or else in the articles by Urdéa et al., (1988) or Sanchez-Pescador et al. (1988).

According to another of its aspects, the present invention relates to the use of the means of detection defined above, for detecting plants resistant/sensitive to at least one potyvirus.

In accordance with the invention, the MvnI and/or TspRI restriction sites, which are incidentally known, of the eIF4E sequences are used as oligonucleotide marker(s) for potyvirus resistance/sensitivity.

Preferably, the restriction sites used as oligonucleotide marker(s) correspond:
to the sense sequence: CG^CG and to the antisense sequence: GC^GC
and/or the sense sequence: NNCASTGNN^ (SEQ ID NO: 24) and to the antisense sequence ^NNGTSACNN (SEQ ID NO: 25).

The use of these restriction sites as markers (or labels or tags) for potyvirus resistance on expressed sequences ties up with the first embodiment of the method of detection described above, in which use is made of restriction enzymes (for example: MvnI and/or TspRI) and of primers for amplification of the eIF4E sequence, for example: SEQ ID NO: 18 and/or 19.

Considering the specificity of the MvnI & TspRI restriction sites, the present invention also encompasses the sue, as oligonucleotide marker(s) for potyvirus resistance/sensitivity, of the abovementioned MvnI & TspRI restriction sites and, preferably, of the restriction site corresponding to the sense sequence: CG^CG and to the antisense sequence GC^GC and/or of the restriction site corresponding to the sense sequence: NNCASTGNN^ (SEQ ID NO: 24) and to the antisense sequence ^NNGTSACNN (SEQ ID NO: 25).

According to another of its aspects, the present invention relates to a kit for selecting potyvirus-resistant/sensitive plants, comprising at least one means of detection of antibody or polynucleotide type as defined above. The kit comprises, where appropriate, the reagents required for carrying out a hybridization or amplification reaction.

A subject of the invention is also the plants derived from the method described above and/or from the implementation of the tools and/or of the use and/or of the selection kit defined above. Preferably, these plants belong to the family of the Solanaceae, Cucurbitaceae, Cruciferae and Compositae. Even more preferably, they are chosen from tomatoes, capsicums and/or lettuce.

By way of examples, the inventors carry out the method which is the subject of the invention by following the protocol for RFLP analysis (restriction fragment length polymorphism). To do this, the inventors have used a conventional RFLP protocol in which the probes which are the subject of the invention are labeled with $^{32}P$ and in which the DNA from the *capsicum* plants to be analyzed is digested with the EcoRI restriction enzyme. At the end of this method, the inventors obtain hybridization profiles which are different between the potyvirus-resistant plants and the potyvirus-sensitive plants, thus making it possible to select the sensitive or resistant plants. The latter may then enter into a program of plant improvement by successive crossing.

The invention does not concern only the selection of plants resistant or sensitive to potyviruses. In fact, insofar as the inventors have been able to identify the eIF4E gene determining a recessive resistance to potyviruses, it is from now on possible to envision obtaining new varieties of genetically modified plants that are resistant (or sensitive) to at least one potyvirus.

The invention therefore relates to a nonbiological method for obtaining new varieties of genetically modified plants that are resistant (or sensitive) to at least one potyvirus, characterized in that it consists essentially in seeing to it that an eIF4E allele associated with resistance (or with sensitivity) to said potyvirus appears in the genome of these plants, and/or in introducing said allele into the genome of these plants.

According to an advantageous embodiment of this method, the appearance of the resistance allele is brought about by implementing a method selected from the group comprising:
mutagenesis, advantageously "tilling",
homologous recombination,
overexpression,
insertion/deletion,
gene silencing/transgenesis,
and combinations thereof.

The tools which may be used in the abovementioned nonbiological method of production also form an integral part of the present invention.

A subject of the present invention is thus any constructed genetic unit comprising a polynucleotide in accordance with the invention encoding a mutant eIF4E protein, placed under the control of suitable elements for controlling the transcription and, optionally, the translation.

Said mutant eIF4E protein can advantageously be chosen from the variants of the sequences SEQ ID NO: 22 or 23 associated with potyvirus resistance.

A subject of the present invention is also any constructed genetic unit, characterized in that it comprises:
at least one genetic tool A/ and/or B/ as defined above,
and/or at least one nucleotide sequence chosen from the group comprising all or part of the following sequences:
SEQ ID NO: 6
SEQ ID NO: 8,
and/or at least one nucleotide sequence encoding an eIF4E factor and comprising at least one MvnI and/or TspRI restriction site, and preferably at least one restriction site corresponding to the sense sequence: CG^CG and to the antisense sequence: GC^GC and/or a restriction site corresponding to the sense sequence: NNCASTGNN^ and to the antisense sequence: ^NNGTSACNN.

Another tool for genetic transformation covered by the invention consists of any vector for transforming plant cells, comprising at least one constructed genetic unit as mentioned above. It may be any known and appropriate cloning vector (phages, plasmids, cosmids, etc.).

The plant cells and the microorganisms transformed by means of at least one vector or of at least one constructed genetic unit as defined above are also part of the invention.

At a higher level, the invention encompasses the plants transformed by means of at least one vector and/or of at least one constructed genetic unit and/or of transformed plant cells and/or of transformed microorganisms, as they have been described above.

Those skilled in the art are very aware of all the direct or indirect techniques for genetic modification. Additional details are given in the examples which follow.

DESCRIPTION OF THE FIGURES

FIG. 3 represents the alignment of the eIF4E protein sequence from various capsicum varieties that are sensitive or resistant to potyviruses. The sequences of these variants are shown by SEQ ID NO: 26 and by the specific SEQ ID NOS mentioned below. In FIG. 3:

Figure 1:
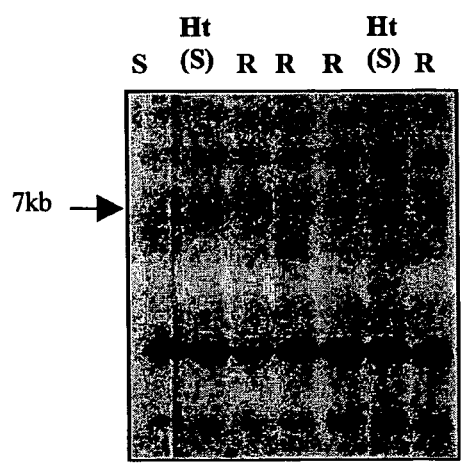
FIG. 1 represents the gel derived from a Southern blotting analysis and showing the differences in profiles of the eIF4E marker for potyvirus resistance, observed for various sensitive or resistant capsicums. The *capsicum* genomic DNA is digested with the EcoRI enzyme and hybridized with the tobacco eIF4E cDNA—SEQ ID NO: 2—(example 3).

the sequence named "YW" corresponds to SEQ ID NO: 7;
the sequence named "YY" corresponds to SEQ ID NO: 9; and
the sequences named "DDL" (SEQ ID NO: 27), "PM1008" (SEQ ID NO: 28), "Avelar" (SEQ ID NO: 29), "Vania" (SEQ ID NO: 30), PM994" (SEQ ID NO: 31), "Florida" (SEQ ID NO: 32), "C69" (SEQ ID NO: 33), "CM334" (SEQ ID NO: 34), PM1014" (SEQ ID NO: 35), and "Per" (SEQ ID NO: 36) respectively refer to SEQ ID NOS: 27-36.

FIG. 4 represents the alignment of the eIF4E protein sequence from various tomato varieties that are sensitive or resistant to potyviruses. Mospo=Mospomorist; PI13=PI134417; PI24=PI247087. Mospo is shown in SEQ ID NO: 5. PI13 is explicitly shown in SEQ ID NO: 23, while PI24 is identified by the variants in SEQ ID NO: 23.

Bold and underlined: mutation observed only in PI247087; in bold not underlined: mutation inter-specific between *L. esculentum* and *L. hirsutum*.

DETAILED DESCRIPTION OF THE INVENTION

Examples

Example 1

Obtaining Tomato and *Capsicum* Probes

The tomato and *capsicum* cDNAs were obtained by the 3' and 5' RACE technique (system for Rapid Amplification of cDNA Ends sold by the company Invitrogen™), from tomato and *capsicum* total RNA extraction, and using degenerate primers defined on the basis of an alignment of the eIF4E sequences from tobacco, tomato and *Arabidopsis*. The 3' portion of the cDNA was cloned by 3'RACE. Defined primers between the TAG and the polyA tail of the sequences obtained by 3'RACE were used to obtain the complete cDNAs by 5'RACE.

```
Primers used for the two steps of the 3' RACE:
Step 1:
TCTAGATACAAYAATATCCAYCACCCAAGCAA = SEQ ID NO: 10

Step 2:
TCTAGATGGGRGCAGACTTTCAYTGTTT. = SEQ ID NO: 11
```

The primers used for the three steps of the 5'RACE are illustrated in table I below:

TABLE I

|  | Capsicum | Tomato |
|---|---|---|
| Step1 | GTA TGA GAA ACT AAA CTA = SEQ ID NO: 12 | AAA TGA GAA ACT AAA CTA = SEQ ID NO: 15 |
| Step2 | CAA CTT TTC AGT ACG AAT TGT GTT T = SEQ ID NO: 13 | CTT TCC AGT ACG AAT TGT GTT TCT T = SEQ ID NO: 16 |
| Step3 | TCC GAC ATT GCA TCA AGA ATT ATA C = SEQ ID NO: 14 | CTG CAT CAA GAA CTA TAC GGT GTA A = SEQ ID NO: 17 |

Example 2

Assay for Hybridization and Selection of the Potyvirus-Resistant Plants (Resistance Controlled by the pvr2/pvr1/pvr5 Locus)

Extraction of the DNA from the Plants to be Analyzed

The extraction of the DNA from the plants (Solanaceae, Cucurbitaceae, Cruciferae and Compositae) follows the protocols for standard extraction based on the DNA microextraction protocol of Fulton and Tanksley, 1995

DNA Digestion and Separation on Agarose Gel

The protocol followed uses 2.5 U of enzyme/µg of DNA. The enzyme volume must be less than 10% of the reaction volume. The reaction volume is calculated as a function of the size of the well: it depends on the type of tank and of comb used and on the gel volume (300 ml in general). The volume of the enzyme-specific buffer and the spermidine volume should each represent 10% of the reaction volume:

xµl DNA

1× buffer

1× spermidine (4 mM)

2.5 U of enzyme/µg of DNA qs for $H_2O$ reaction volume.

The digestion is carried out at 37° C. overnight. In parallel, samples of λ phages digested with Hind III are prepared: 0.5 µg/well. After digestion, correct digestion of the DNAs is verified on 1% agarose gel, 1×TAE, with 1 µl of digestion product. If the digestion is correct, the loading buffer is then added. The loading buffer should represent a minimum of 10% of the total volume (or 20%). The sample is then deposited onto a 300 ml, 1% agarose, 1×NEB, gel containing 10 µl of ETB. The migration is carried out at 25 V for 24 h in 1×NEB buffer (the migration is stopped at 2 cm from the edge of the gel).

Transfer onto Nylon Membrane

A Hybond N+ membrane and 1 Whatman paper are cut to the size of the gel. The gel is soaked for 30 min in a flat tank containing 1 L 0.25N HCl, with agitation (the blue becomes yellow).

During this time, the blotter is prepared by:

wetting a sheet of Whatman paper into 2×SSC and placing it on the porous plate of the blotter;

and then by wetting the membrane and placing it on the Whatman, which will be covered with the plastic screen.

The gel is rinsed in a tank containing distilled $H_2O$, and then placed on the screen of the blotter, avoiding bubbles, and checking that the system is leaktight. The blotter is switched on at a maximum of 50 mb. Some 0.4N probe is poured over the gel. Two sponges soaked in sodium hydroxide are placed on the gel, which will be covered with sodium hydroxide until saturation is obtained.

The transfer is carried out in 2 h to 3 h. The membranes are rinsed in a bath of 2×SSC for 10 to 15 min and then dried in the open air and baked for 2 h at 80° C.

Probe Preparation

Preparation of the probes by PCR labeling with $^{32}P$ involves probes of no more than 3 kb, amplified by PCR or directly on plasmids, making it possible to reveal the major bands for a probe of concentration between 1 and 5 ng/µl.

The reaction conditions are summarized in table 2 below.

TABLE 2

|  | Final concentration |  |
|---|---|---|
| H$_2$O | 25.6 µl |  |
| Promega 10× buffer | 4 µl | 1× |
| Promega MgCl$_2$ | 2.4 µl |  |
| Mix (50 µM ATG + 5 µM dCTP) * | 2 µl | 2.5 µM ATG; 0.25 µM dCTP |
| 2 U/µl Taq | 1 µl |  |
| Primer (5 pM) | 1 µl |  |
| α32P-dCTP (1000 Ci/mmol, 10 µCi/µl) | 3 µl |  |
| DNA probe | 1 µl |  |
| Final reaction volume | 40 µl |  |

*: Mix (50 µM ATG + 5 µM dCTP) for labeling the RFLP probes by PCR.

Dilution of dATP, dTTP, dGTP to 10 mM, from the 100 mM stock solutions:
5 µl dNTP at 100 mM
45 µl H$_2$O.
Dilution of dCTP to 1 mM, from the 100 mM stock solution:
0.5 µl dCTP at 100 mM
49.5 µl H$_2$O.
Mix ATG+dCTP:
2.5 µl dATP at 10 mM, final concentration: 50 µM
2.5 µl dTTP at 10 mM, final concentration: 50 µM
2.5 µl dGTP at 10 mM, final concentration: 50 µM
2.5 µl dCTP at 1 mM, final concentration: 50 µM
490 µl H$_2$O.
The probes are labeled over the course of 30 PCR cycles of:
30 s at 94° C.
45 s at 52° C.
1 min 30 s at 72° C.
Once labeled, the probes are then denatured according to the following protocol:
each probe is added to a tube containing 160 µl of 0.8N NaOH+2 to 5 µl of labeled (by random priming) lambda
incubation is carried out for 5 min
neutralization is carried out with 200 µl of 1M Tris HCl.
Hybridization
Protocol According to Church and Gilbert (1984)
a—Prehybridization at 65° C. Overnight
20 ml of hybridization buffer are used per tube for 2 to 6 half-blots. Beyond this, 25 ml of buffer are used, without exceeding 10 half-blots per tube. The membranes are wetted in a dish containing hybridization buffer before being slightly drained and then rolled up (altogether) and placed in the tube.
*Composition of the Prehybridization and Hybridization Buffer:
During prehybridization, it is verified that the tubes are leaktight and that the membranes unroll correctly, otherwise their direction is changed.
For 500 ml: 21.91 g NaCl; 18.38 g sodium citrate; 380 ml H$_2$O; 15 ml 20% SDS; 25 ml 1M NaPO$_4$, pH 7.5; 25 ml 100×Denhardt's; 5 ml 0.25M EDTA; 50 ml 50% dextran sulfate.
b—Hybridization at 65° C. for at Least 16 Hours
The temperature of the tubes is allowed to decrease before opening them in order to avoid wetting the thread. The denatured probe (5 min in 0.8M NaOH and then denaturation is stopped with 1M Tris-HCl) is added. Under these conditions, the hybridization can last 48 or 72 hours.
c—Washing
The dishes (or trays) are washed in a large excess of buffer (1% SDS (Serva)) containing 40 mM NaPi, preheated to 65° C. For approximately 5-10 half-membranes:
1 wash for 20 min at 65° C. with agitation. To wash, membranes are transferred one by one into a new tray containing the preheated buffer. The radioactive washing buffers (at least the first 2) are poured into a flask provided for this purpose;
1 rinse for 2-3 min in new buffer heated to 65° C.
d—Exposure
The membranes are dried on a bed of absorbent paper consisting of an area of blue paper covered with white paper such as a roll of Tork paper; they must not dry out. They are then placed in small plastic bags for the exposure, placed in a cassette with 1 intensifying screen.
According to the signal measured with a Geiger counter, they are exposed at −80° C. for a period of overnight to a few days.
e—Dehybridization of the Membranes Before Rehybridization
The membranes are dehybridized in a 0.1% SDS, 1 mM EDTA solution heated to 80° C. (1 liter for 40 half-membranes) for 20 min at ambient temperature. The membranes are then rinsed for 10 min in a 2×SSC solution. Finally, the membranes are partially dried and then stored damp in small plastic bags at 4° C.

Example 3

Correlation Between Potyvirus Resistance and eIF4E

The viral material used in these infection assays are the PVY N-605 isolates obtained from *Solanum tuberosum* (Jakab et al., 1997), or PVY-LYE84 or PVY-LYE240r for tomato (Legnani et al., 1995) and the PVY-To72 and PVY-Si15 isolates for *capsicum* (Dogimont et al., 1996) and also the TEV CAA-10 isolate (Legnani et al., 1996). The same protocol is used for all the other PVY and TEV isolates which are controlled by the pvr2/pyr1/pvr5 and/or pot-1 loci. The isolates are maintained according to the Bos procedure (Bos, 1969) and multiplied on *Nicotiana tabacum* cv. *Xanthii* plants before inoculation of the tomato or *capsicum* plants at the stage of cotyledons with two leaves with horizontal blades. The viral inoculum is prepared as described in the articles by Legnani et al. (1995, 1996) and by Dogimont et al. (1996). The cotyledons and the first two leaves of the plants are inoculated mechanically. The lines are evaluated under controlled conditions in a growth chamber (14 hours of day time, 18° C. night and 24° C. day) in order to monitor their reaction after inoculation. 4 weeks after inoculation, all the plants are evaluated individually for the presence or the absence of the PVY or TEV capsid antigen using an ELISA assay (enzyme linked immunosorbent assay) as described by Legnani et al., 1995, 1996) and Dogimont et al. (1996). Other protocols which are entirely known to those skilled in the art can also be used for the mechanical inoculation of plants with potyviruses.

The gel presented in FIG. 1 in the appendix shows the difference in profiles observed between the eIF4E marker and the resistance to potyviruses controlled by the pvr2 locus. This complete cosegregation between potyvirus resistance and a copy of the eIF4E gene was observed on a linage by segregation of more than 500 plants.

The *capsicum* genomic DNA is digested with the EcoRI enzyme and hybridized with the tobacco eIF4E cDNA—SEQ ID NO: 2—(the same RFLP profiles are obtained by hybridization with the tomato cDNA or the *capsicum* cDNA).

The sensitive (S) plants possess the "lower" 7 kb restriction fragment whereas the resistant (R) plants possess the "upper"

7 kb restriction fragments. The heterozygotes (Ht) plants exhibit the two restriction fragments and are sensitive (because of recessive gene).

Example 4

Demonstration of eIF4E Mutations Associated with Potyvirus Resistance

1) Demonstration of Differential Restriction Sites Between the Copies of a Potyvirus-Sensitive *Capsicum* Genotype and of a Resistant Genotype Point mutations between the eIF4E gene of the *capsicum* variety "Yolo Wonder" (sensitive to potyvirus and carrying the pvr2+ allele) and that of the *capsicum* variety "Yolo Y" (potyvirus resistant and carrying the pvr2[1] allele) were demonstrated by conventional sequencing techniques. Thus, at position 200, the coding sequence SEQ ID NO: 6 of eIF4E in Yolo Wonder exhibits a T, whereas the coding sequence SEQ ID NO: 8 of eIF4E in Yolo Y exhibits an A. Similarly, at position 236, the coding sequence of Yolo Wonder exhibits a T, whereas the coding sequence of Yolo Y exhibits a G.

The first point mutation corresponds to a TspRI restriction site (or its isoschizomers) which exist only in Yolo Wonder. This differential restriction site was validated by PCR on the Yolo Wonder and Yolo Y cDNA: definition of primers in the 5'- and 3'-position of the cDNA and digestion of the PCR-amplified material with the TspRI enzyme.

(Same protocol as above for the MvnI enzyme, except that the digestion is carried out at 70° C. for this enzyme).

The second point mutation corresponds to an MvnI restriction site (or its isoschizomers) which exists only in Yolo Y. This differential restriction site was validated by PCR on the Yolo Wonder and Yolo Y cDNA: definition of primers in the 5'- and 3'-position of the cDNA and digestion of the PCR-amplified material with the MvnI enzyme.

```
PCR reaction on the cDNA:
sense primer:
AAA AGC ACA CAG CAC CAA CA = SEQ ID NO: 18 antisense primer:
TAT TCC GAG ATT GCA TCA AGA A = SEQ ID NO: 19
```

The reaction conditions are as given in table 3 below.

TABLE 3

|  | Final concentration |
|---|---|
| H$_2$O | 13.05 µl |
| Promega 10× buffer | 2.5 µl 1× |
| Promega MgCl$_2$ | 2.0 µl |
| dNTP (4 µM) | 1.25 µl |
| 2 U/µl Taq | 1 µl |
| Primer (10 pM) | 1.5 µl of each |
| cDNA (10 ng/µl) | 3 µl |
| Final reaction volume | 25 µl |

Amplification cycles: 93° C.-3 min/35× (93° C.-45 s/53° C.-1 min/72° C.-2 min/72° C.-10 min Digestion with the MvnI enzyme: 8 µl of PCR product+2 U of enzyme+1.3 µl of enzyme buffer+13.5 µl H$_2$O 2 h at 37° C. Migration on a 1×TAE 1.2% agarose gel.

Figure 2:
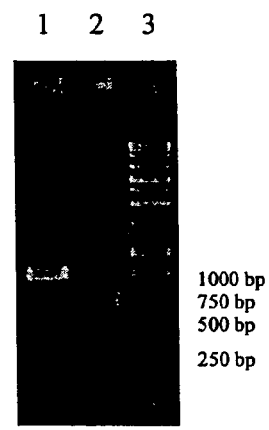
FIG. 2 represents the gel showing the PCR amplifications of the eIF4E gene involved in potyvirus resistance in *capsicum*, and demonstrates an MvnI restriction site which is differential between sensitive and resistant (example 4).

The gel presented in FIG. 2 in the appendix shows the PCR amplifications of the eIF4E gene involved in potyvirus resistance in the *capsicum* and demonstrates an MvnI restriction site that is differential between sensitive and resistant.

Band 1:
PCR-amplified material of the eIF4E gene of the potyvirus-sensitive (S) *capsicum* Yolo Wonder-pvr2+ allele, and absence of enzymatic digestion with MvnI.
Band 2:
PCR amplified material of the eIF4E gene of the potyvirus-resistant (R) *capsicum* Yolo Y-pvr2[1] allele, and demonstration of the MvnI restriction site.
Band 3:
1 kb ladder size marker.

2) Demonstration of eIF4E Mutations Associated with Potyvirus Resistance

Sequencing of the eIF4E gene of various potyvirus-sensitive or potyvirus-resistant *capsicum* varieties revealed mutations, associated with potyvirus resistance, in the same region of eIF4E.

Alignment of the eIF4E protein sequence of the various varieties is represented in FIG. 3.

Legend of FIG. 3:
YW=Yolo Wonder S/pvr2+
DDL=Doux Long des Landes S/pvr2+
PM1008=resistant to PVY(0)
YY=Yolo Y/pvr2[1]
Avelar=pvr2[1] allele
Vania=pvr2[1] allele
PM994=resistant to PVY(0)
Florida VR2=Florida/pvr2[2]
C69=HD line derived from the F1 hybrid between CM334 and Yolo Wonder/pvr5
CM334=Criollo de Morelos 334/pvr5
PM1014=resistant to PVY(0)
Per=perennial/partial resistance (QTL) at the pvr2 locus
Bold underlined=mutation common to all the resistants except PM1008
Highlighted in gray=mutation specific to the pvr2[1] allele
Bold not underlined=mutation specific to the pvr2[2] allele
Underlined not bold=mutation specific to the pvr5 allele
Highlighted in black=mutation specific to the PM1008 genotype.

These various variants are also represented in the sequence SEQ ID NO: 22

Example 5

Demonstration of the Synteny Between *Capsicum* and Tomato for the Recessive Genes for Potyvirus Resistance (pot-1 Gene in Tomato and pvr2 Locus in *Capsicum*)

Five main genes and several QTLs involved in potyvirus resistance are mapped on the *capsicum* genome. By means of the use of common RFLP probes for mapping the genome and due to the highly conserved nature of order of the markers between the tomato genome and the *capsicum* genome, the potyvirus-resistance factors for *capsicum* are placed on the tomato map. The location of the *capsicum* potyvirus-resistance loci on the tomato chromosomes, and also that of the associated RFLP markers, is recapitulated in table 4 with the references of origin. With the aim of precisely establishing the correspondence between the genomic regions of *capsicum* and of tomato with the potyvirus-resistance genes, the TG135 and Cab3 RFLP markers are added to the pre-existing genetic linkage map for *capsicum* (Lefebvre et al., submitted).

TABLE 4

| Gene | Spectrum | Associated markers[b] | Chromosomal position in tomato | Reference |
|------|----------|----------------------|-------------------------------|-----------|
| pvr1 | TEV, PepMoV[a] | TG56, TG135 | 3 | Murphy et al. 1998 |
| pvr2 | PVY, TEV[a] | CT31, TG132 | 3 | Caranta et al. 1997 Caranta et al., unpublished |
| pvr3 | PepMoV[a] | nd[c] | nd[c] | Murphy et al. 1998 |
| pvr4 | PVY, PepMoV | CD72, CT124 | 10 | Caranta et al. 1999 Grube et al. 2000 |
| pvr5 | PVY[a] | CT31 | 3 | Caranta et al., unpublished |
| pvr6 | PVMV | TG57 | 9 | Caranta et al. 1996 |
| pvr7 | PepMoV, PVY[a] | CD72, CT124 | 10 | Grube et al. 2000 |

[a]Only the general spectrum of resistance is indicated for each gene, some of these resistance genes can be circumvented by virulent strains.
[b]The RFLP markers are obtained using randomly tomato genomic (TG) DNA or tomato leaf epidermis cDNA probes (CD and CT).
[c]nd = not determined a—AFLP and RFLP Labeling of the pot-1 Gene The total DNA is extracted from approximately 1 g of fresh leaves from F2 plants (Caranta et al., 1997).

The DNA samples from 6 F2 plants (derived from self-fertilization of the F1 hybrid between *Lycopersicon esculentum* Mospomorist and *L. hirsutum* PI247087) (pot-1+/pot-1+) having generated F3 families completely sensitive to PVY strain N 605 and the DNA samples from 9 F2 plants having generated F3 families completely resistant to potyvirus are grouped together for a bulked segregant analysis and for AFLP tagging of pot-1.

The AFLP markers are generated according to the protocol by Vos et al. (1995) with the EcoRI, HindIII and MseI restriction enzymes. The first amplification is carried out using a combination of primers with a single selective nucleotide and a second combination with 3 selective nucleotides.

The AFLP markers associated with pot-1 are mapped on the lines produced from introgression of *L. hirsutum* into *L. esculentum* (Montforte and Tanksley, 2001) in order to assign pot-1 to a tomato chromosome.

This assignation is validated by the mapping of RFLP markers located on the target chromosome. The RFLP procedure is described by Saliba-Colombani et al. (2000). The screening of the polymorphism between *Lycopersicon esculentum* Mospomorist (sensitive to potyvirus) and *L. hirsutum* PI247087 (resistant to potyvirus) is carried out with 3 restriction enzymes (EcoRI, HindIII and XbaI) and RFLP markers pre-mapped in tomato (CT, tomato cDNA derived from tomato epidermal tissue mRNA; TG, tomato genomic DNA clones; the CAB3 probe encoding a chlorophyll a/b binding polypeptide, Tanksley et al., 1992). The screening makes it possible to map additional markers on chromosome 3.

Segregation analysis for the molecular markers (AFLP, RFLP) and for the resistance data are carried out using the Mapmaker/Exp v. 3.0 software with a minimum Lod of 4.0 and a maximum recombination percentage of 0.3. The recombination percentage is then converted into mapping distance in centiMorgans (cM) using the Kosambi mapping function (Kosambi, 1944).

These results made it possible to locate the pot-1 gene for PVY resistance in tomato on chromosome 3 and to show that this gene is bordered by the same RFLP markers as the pvr2 locus in *capsicum*.

b—Mapping of eIF4E in Tomato

In parallel, the tomato eIF4E cDNA was mapped by the RFLP method described above on the lines produced from introgression of *L. pennellii* into *L. esculentum* (Eshed and Zamir, 1995). This study made it possible to locate 5 copies of the eIF4E gene in tomato. One of these copies was located on chromosome 3, in the same genomic region as the pot-1 gene, thus confirming the synteny between *capsicum* and tomato for potyvirus resistance and, consequently, the possibility of using eIF4E as markers and tools for selecting resistance.

This demonstration of synteny between *capsicum* and tomato for the recessive genes for potyvirus resistance makes it possible to say that, if eIF4E is the resistance gene in *capsicum*, then eIF4E is also the resistance gene in tomato.

c—Cloning of a Tomato eIF4E Gene Associated with Potyvirus Resistance cDNA of a tomato eIF4E gene similar to that isolated in *capsicum* was isolated and cloned in tomato, according to the 3' and 5' RACE PCR method described in example 1; this gene was called eIF4E-2.

The coding sequence of this gene (variety 'Mospomorist' of *L. Esculentum*, sensitive to PVY and to TEV) is represented in the sequence listing under the number SEQ ID NO: 2.

Point mutations between the eIF4E-2 gene of the *L. esculentum* 'Mospomorist' and *L. hirsutum* PI134417 tomato genotypes (sensitive to PVY and TEV) and that of the *L. hirsutum* PI247087 genotype (resistant to PVY and to TEV, resistance controlled by the pot-1 recessive gene) were demonstrated using conventional sequencing techniques.

The sequence alignment in represented in FIG. 4.
Legend: Mospo=Mospomorist; PI13=PI134417; PI24=PI247087

Bold and underlined: mutation observed only in PI247087; in bold not underlined: mutation inter-specific between *L. esculentum* and *L. hirsutum*.

The eIF4E protein of *L. hirsutum* PI134417 and that of *L. hirsutum* PI247087 are also represented by the sequence SEQ ID NO: 23.

Example 6

Screening of the *capsicum* Genome BAC Library with Primers Defined on the eIF4E Coding Sequence of the Yolo Wonder Genotype, Demonstration of the Cosegregation with Resistance and Determination of the Genomic Structure of the eIF4E Gene which Cosegregates with pvr2

A *capsicum* BAC library was constructed from a doubled haploid line HD208 derived from the F1 hybrid of a cross between *Capsicum annuum* Yolo Wonder and *C. annuum* perennial. HD208 contains the pvr2+ dominant allele sensitivity.

The high molecular weight DNA was extracted according to the method described in http://www.ncgr.org/research/jag/papers00/paper300/indexpage300.html. The DNA was then partially and separately digested with three restriction enzymes (EcoRI, BamHI and HindIII) in order to increase the representativeness of the entire genome. The digestive DNA was cloned into the vector pCUGIBAC1.

The *capsicum* BAC library consists of 239 232 clones with an average insert size of 125 kb, which corresponds to a theoretical representativity of 10 genome equivalents (size of the *capsicum* genome 3000 Mpb). This BAC library was organized into 623 DNA pools for the purpose of screening by PCR (1 pool corresponds to a mixture of DNA from 384 clones).

The following primers were defined on the coding sequence of eIF4E from Yolo Wonder:

```
Pim1:   5' AGA CTT TCA TTG TTT CAA GCA TAA 3' =
        SEQ ID NO: 20

Pim4:   5' GAT TAG AAA GTG CAA ACA CCA ATA C 3'. =
        SEQ ID NO: 21
```

This pair of primers amplifies a 493 bp band on the cDNA and an 1800 bp band on the HD208 genomic DNA. This pair of primers was used to screen the *capsicum* BAC library. Four BAC clones were identified carrying the 1800 bp band (clones 27-BI, 5-2H, 111-4H and 184-4H).

These four BAC clones were digested with EcoRI and the restriction profiles show that they overlap and therefore clearly correspond to the same locus. All the BAC clones reveal an EcoRI band of 7 kb, which was cloned into a vector pGEM3Zf. This 7 kb band, obtained by EcoRI digestion, corresponds to that which co segregates with potyvirus sensitivity (see example 3).
(1=clone 27-BI; 2=clone 5-2H; 3=clone 111-4H; 4=clone 184-4H)

The presence of the 1800 bp amplified material in the 7 kb fragment confirms that these four BAC clones carry the eIF4E gene corresponding to the cloned cDNA. Sequencing of the 7 kb insert made it possible to define the size of the gene, which is 5500 bp, and to define the exon/intron structure: 5 exons and 4 introns.

Example 7

Experiment Comprising Transient Expression of the Yolo Wonder eIF4E cDNA in a Resistant *capsicum* Genotype (Carrying the pvr21 Allele) for Validation of the Role of eIF4E in Potyvirus Sensitivity In order to validate the hypothesis that the pvr2+ sensitivity allele corresponds to the Yolo Wonder eIF4E gene, experiments comprising transient expression of the Yolo Wonder eIF4E cDNA via a PVX (potato virus X) viral vector (Chapman et al., 1992) are carried out on a Yolo Y resistant genotype, carrying the pvr2$^1$ allele.

The eIF4E cDNA derived from the Yolo Wonder sensitive genotype is cloned in an oriented manner into an expression vector PVX-CES-35S at the ClaI and SalI cloning site.

The Yolo Y resistant genotype (carrying the pvr2$^1$ allele) is co-inoculated with this recombinant plasmid and with the potato virus Y (PVY) pathotype 0. Transient expression of the eIF4E gene derived from the Yolo Wonder sensitive genotype via the recombinant PVX vector makes it possible for PVY to multiply in the resistant genotype. The PVY is detected by the ELISA or RT-PCR method (Legnani et al., 1995, 1996, Dogimont et al., 1996).

The two genotypes of *C. annuum* Yolo Wonder and Yolo Y which have received the recombinant plasmid are sensitive to PVY: the viruses detected by ELISA and RT-PCR on inoculated leaves and systemic leaves 10 days after inoculation.

Similarly, eIF4E alleles derived from Yolo Wonder and Yolo Y, which are both sensitive to TEV (tobacco etch virus), were expressed in a TEV-resistant *capsicum* genotype: Florida VR2. It is observed that this expression allows TEV to multiply (detected by ELISA and RT-PCR) in this resistant genitor.

The tomato eIF4E-2 cDNA obtained from the variety Mospomorist (carrying the sensitivity allele SEQ ID NO: 4) was also expressed according to the same protocol in the Yolo Y resistant *capsicum* genotype.

Restoration of the sensitivity to PVY of the Yolo Y *capsicum* expressing the tomato eIF4E-2 cDNA is also observed.

These results confirm the involvement of eIF4E in the sensitivity to various potyviruses, and also show that this system functions in a heterologous manner (tomato gene which functions in *capsicum*).

Example 8

Search for Mutants in the eIF4E Gene and in the Genes of the RNA Translation Initiation Complex for Creating Potyvirus-Resistant Plants The members of the eIF4E multigene family belong to a complex of at least 8 proteins which form the translation initiation complex in eukaryotic cells (Browning 1996).

The identification and the characterization of mutants in eIF4E and in the other genes of the translation initiation complex, for creating potyvirus-resistant plants, take place in 4 steps and use a TILLING system (Targeting Induced Local Lesions IN Genomes, McCallum et al., 2000):

(1) Generation of a collection of tomato mutants by chemical mutagenesis. The genotype chosen is a microtomato, *Lycopersicon esculentum* Microtom, which exhibits advantageous biological characteristics (Meissner et al., 2000): sensitive to potyviruses (PVY, TEV and PVMV), growth at high density (1000 plants/m$^2$) and generation time of 3-4 months. The mutations are obtained by chemical mutagenesis with ethylmethyl sulfonate (EMS) (Koornneef et al., 1982): mutagenesis on 30 000 seeds, sowing of the mutants and production of the M2 generation from 5000 M1 plants.

(2) Extraction of DNA from 20 plants per M2 family and formation of DNA pools in 3 dimensions from a population of 100 000 M2 plants (5000 families).

(3) PCR amplification of the targeted genes and search for mutations by denaturating HPLC. The sequencing of the genes involved in the translation initiation complex are available on the site http:/www.tigr.org/tdb/lgi. The PCR products are subsequently denatured and then paired so as to allow the formation of heteroduplexes. The mutations are then detected either by denaturing HPLC (McCallum et al., 2000) or by means of an enzyme which allows detection of "mismatches" in the heteroduplex (CEL1 enzyme, Oleykowski et al., 1998).

(4) Characterization of the mutants in order to evaluate their behaviour with respect to potyviruses: change from a sensitive phenotype to a resistant phenotype. The procedure for inoculation and detection of the potyviruses (potato virus Y, tobacco etch virus, pepper veinal mottle virus) is identical to that described in example 3.

Example 9

Creation of Potyvirus-Resistant Plants by Methods which May Involve Transgenesis As an alternative to example 8, the resistance allele of the eIF4E gene (identified here in *capsicum*) or any other eIF4E allele which confers potyvirus resistance (identified on the basis of examples 1 to 8) can be transferred, in planta, by means of methods such as site-directed mutagenesis (Hohn et al., 1999), or homologous recombination (Kempin et al., 1997), or by means of overexpression methods. In the overexpression experiments, the eIF4E allele which confers resistance is expressed under the control of a strong promoter of the CaMV virus 35S type by transgenesis in planta (Jones et al., 1992; Bevan 1984).

Resistant plants can also be created by knock-out of the endogenous eIF4E gene by means of gene silencing-type methods (post transcriptional gene silencing) and the simultaneous expression, by transgenesis, of the eIF4E form which confers potyvirus resistance. A specific knock-out by PTGS can be carried out by directing it against the 5' UTR of the endogenous eIF4E gene; the eIF4E form which confers resistance, expressed by transgenesis, will not carry the 5' UTR sequence of the endogenous eIF4E. This specificity of the knock-out by PTGS against the 5' UTRs is based on the new data derived from the understanding of the PTGS mechanism (Nishikura 2001).

BIBLIOGRAPHY

Altschul et al., 1990, J. Mol. Biol., 215 :403-10
Altschul et al., 1993, J. Mol. Evol., 36:290-300
Bevan et al., 1984, NAR 12, 8711-8721
Bos, 1969, Meded. Fac. Landbouwwet Gent. 34, 875-887
Browning, 1996. Plant Mol. Biol. 32:107-144
Caranta et al., 1997 Molecular Plant-Microbe Interactions 10(7), 872-878
Chapman et al., 1992. Plant J. 2(4):549-557
Church et Gilbert 1984, PNAS 81, 1991-1995
Dogimont et al., 1996. Euphytica 88:231-239
Dougherty et Carrington, 1988. Annual review of Phytopathology 26, 123-143
Flor, 1955. Phytopathol. 45:680-685
Filatti et al., 1987. Bio/Technology 5:726-730
Fraser, 1992. Euphytica 63:175-185
Fulton et Tanksley, 1995.
Hammond-Kosack et Jones, 1997. Ann. Rev. Plant Physiol. Plant Mol. Biol. 48:575-607
Hohn et al. 1999, PNAS 96, 8321-8323
Jakab et al., 1997, Journal of General Virology 78, 3141-3145
Jones et al., 1992, Transgenic research 1, 285-297
Keller et al., 1998. Mol. Plant-Microbe Interact. 11:124-130
Kempin et al., 1997, Nature 389, 802-803
Kohler et Milstein, 1975 Nature 256, 495
Koornneef et al., 1982. Mutat. Res. 93:109.123
Kozbor et al. 1983, Hybridoma 2 (1), 7-16
Langenberg et Zhang, 1997. Journal of Structural Biology 118, 243-247
Légnani et al, 1995 Euphytica 86, 219-226.
Légnani et al, 1996, Plant disease, 80 (3), 306-309
McCallum et al., 2000. Plant Physiol. 123:439-442
McCormick et al., 1986. Plant Cell Reports 5:81-84
Martin et Gelie, 1997. European Journal of Plant Pathology 103, 427-431
Martineau et al., 1998, Journal of Molecular Biology 280 (1), 117-127
Meissner et al., 2000. Plant J. 22:265-274
Morel, 2001. Doctoral Thesis from the University of Rennes 1, 136.
Murphy et al., 1990, Virology 178, 285-288
Nicolas et al., 1997. Virology 237:452-459
Nishikura, 2001, Cell 107, 415-418
Oleykowski et al., 1998. Nucleic Acids Res. 26:4597-4602
Redondo, 2001. Doctoral Thesis from the University Bordeaux 2, 160 pp.
Riechmann et al., 1992. Journal of General Virology 73, 1-16
Rodriguez et al., 1998. Plant J. 13(4):465-473.
Rudd K et al., 1998. J. Biol. Chem. 273 (17): 10325-10330
Sambrook et al., 1989 Molecular Cloning: A Labratory Manual,
Sanchez-Pescador et al., 1988. J. Clin. Microbiol. 26 (10): 1934-1938
Schaad et al., 2000. Virology 273:300-306
Takahashi et al., 1997 Virus genes 14(3), 235-243.
Urdea et al., 1988. Nucleic Acids Research. 11: 4937-4957
Wittman et al. 1997. Virology 234:84-92

The invention claimed is:

1. A method for selecting a plant of the family of Solanaceae containing a gene involved in conferring potyvirus resistance, comprising:
   (A) detecting in a test plant of the family of Solanaceae the presence or the absence of a mutant eIF4E protein or a mutant allele encoding said eIF4E protein, and
   (B) selecting a plant in which a mutant eIF4E protein, or a mutant allele encoding said mutant eIF4E protein, is detected;
   wherein said mutant eIF4E protein
   contains the substitution of a neutral amino acid residue at least one position selected from the group consisting of position 2, 3, 4, 5, 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44 and 45 of SEQ ID NO: 1 with a charged amino acid, or
   the substitution of a charged amino acid residue at least one position selected from the group consisting of position 1, 6, 8, 17, 26, 27, 36, 37, 40 and 46 of SEQ ID NO: 1 with a neutral amino acid or an amino acid having an opposite charge.

2. The method of claim 1, wherein said mutant eIF4E protein comprises at least one of the following mutations within the region defined by the sequence of SEQ ID NO: 1:
   a) the substitution of an amino acid at least one position selected from the group consisting of position 2, 3, 4, and 5 of said sequence SEQ ID NO: 1 with a charged amino acid, and
   b) the substitution of a neutral amino acid at least one position selected from the group consisting of position 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44, and 45 of SEQ ID NO: 1 with a charged amino acid or substitution of a charged amino acid at least one position selected from the group consisting of position 1, 6, 8, 17, 26, 27, 36, 37, 40, and 46 of SEQ ID NO: 1 with a neutral amino acid or an amino acid having an opposite charge.

3. The method of claim 1, further comprising
   selecting a potyvirus-resistant plant in which a mutant eIF4E protein, or a mutant allele of the eIF4E gene encoding said protein is detected, and no wild-type eIF4E protein or wild-type allele of the eIF4E gene encoding said wild-type eIF4E protein is detected.

4. The method of claim 1, wherein the presence or absence of said mutant allele of the eIF4E gene is detected using a nucleotide probe corresponding to all or part of a mutant polynucleotide sequence of SEQ ID NO: 8.

5. The method of claim 3, wherein the presence or absence of said wild-type allele of the eIF4E gene is detected using a nucleotide probe corresponding to all or part of a wild-type polynucleotide sequence of SEQ ID NO: 2, 4, or 6.

6. The method of claim 3, wherein the wild-type eIF4E protein is the protein represented by the polypeptide of sequence SEQ ID NO: 3.

7. The method of claim 3, wherein the wild-type allele of the eIF4E gene is the polynucleotide of sequence SEQ ID NO: 2.

8. The method of claim 3, for selecting a potyvirus-resistant plant, comprising:
   amplifying the coding sequence of the eIF4E gene by PCR from DNA of the plant to be tested;
   digesting the amplification product with the MvnI restriction enzyme or one of its isoschizomers and the TspRI enzyme or one of its isoschizomers;
   selecting the plant having a restriction profile for said amplification product which reveals the presence of a site for cleavage with MvnI, and the absence of a site for cleavage with TspRI, wherein said plant is a potyvirus resistant plant.

9. The method as claimed in claim 8, wherein the PCR amplification of the coding sequence of the eIF4E gene is carried out using, as primers, the oligonucleotides SEQ ID NO: 18 and SEQ ID NO: 19.

10. A method for identifying a plant that is resistant to a potyvirus comprising:
   (A) detecting in a test plant of the family Solanaceae selected from the group consisting of tomatoes or peppers (capsicum) at least one mutation to a wild-type eIF4E protein in a mutant plant compared to the corresponding wild-type plant,
   wherein said wild-type eIF4E protein comprises SEQ ID NO: 1; and wherein said at least one mutation in the wild-type eIF4E protein is the substitution of a neutral amino acid at least one position selected from the group consisting of position 2, 3, 4, 5, 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44 and 45 of SEQ ID NO: 1 with a charged amino acid, or the substitution of a charged amino acid at at least one position selected from the group consisting of position 1, 6, 8, 17, 26, 27, 36, 37, 40 and 46 of said SEQ ID NO: 1 with a neutral amino acid or an amino acid having an opposite charge; and (B) selecting a mutant plant having increased resistance to a potyvirus compared to the corresponding wild-type plant expressing a wild-type eIF4E protein comprising SEQ ID NO: 1.

11. The method of claim 3, which comprises detecting the presence or absence of a mutant eIF4E protein that comprises the following mutations within the region defined by the sequence SEQ ID NO: 1:

a) the substitution of at least one of the an amino acid at least one position selected from the group consisting of position 2, 3, 4 and 5 of said sequence SEQ ID NO: 1 with a charged amino acid, and b) the substitution of a neutral amino acid at least one position selected from the group consisting of position 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44 and 45 of SEQ ID NO: 1 with a charged amino acid or substitution of a charged amino acid at least one position selected from the group consisting of 1, 6, 8, 17, 26, 27, 36, 37, 40 and 46 of SEQ ID NO: 1 with a neutral amino acid or an amino acid having an opposite charge.

12. A method for selecting a plant that is resistant to potyvirus infection comprising:

(A) modifying the sequence of the eIF4E gene of a wild-type plant of the family Solanaceae that is not resistant to potyvirus infection to produce a mutant plant, and (B) selecting a plant that is resistant to potyvirus infection compared to the unmodified wild-type plant;

wherein the eIF4E gene of the wild-type plant encodes a polypeptide comprising SEQ ID NO: 1 and the mutant plant expresses a mutant eIF4E polypeptide that contains at least one mutation within SEQ ID NO: 1 which is:

the substitution of a neutral amino acid at one or more positions selected from the group consisting of positions 2, 3, 4, 5, 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44 and 45 of said SEQ ID NO: 1 with a charged amino acid, or the substitution of at least one charged amino acid at one or more positions selected from the group consisting of positions 1, 6, 8, 17, 26, 27, 36, 37, 40 and 46 of said SEQ ID NO: 1 with a neutral amino acid or an amino acid having an opposite charge.

13. The method of claim 12, wherein the mutant eIF4E polypeptide consists of the same sequence as the wild-type eIF4E polypeptide, except that it has a substitution at least one position selected from the group consisting of residues 2, 3, 4, 5, 10, 16, 18, 19, 24, 30, 31, 42 and 43 of SEQ ID NO: 1 with a neutral amino acid selected from the group consisting of alanine, valine, leucine, isoleucine, phenylalanine, methionine, glycine, serine, threonine, tyrosine, cysteine, glutamine, and asparagine; or with a charged amino acid residue selected from the group consisting of histidine, lysine, arginine, glutamate, and aspartate.

14. The method of claim 13, wherein the mutant eIF4E polypeptide consists of the same sequence as the wild-type eIF4E polypeptide, except that it has a substitution of at least one of said neutral amino acid at residues 2, 3, 4 or 5 of SEQ ID NO: 1 with at least one of said charged amino acid(s) residues.

15. The method of claim 12, wherein the mutant eIF4E polypeptide consists of the same sequence as the wild-type eIF4E polypeptide, except that it has a substitution at least one of residues 8 or 37 of SEQ ID NO: 1 with a charged amino acid residue selected from the group consisting of histidine, lysine and arginine, with a neutral amino acid selected from the group consisting of alanine, valine, leucine, isoleucine, phenylalanine, methionine, glycine, serine, threonine, tyrosine, cysteine, glutamine, and asparagine; or with an acidic amino acid selected from the group consisting of glutamate and aspartate.

16. The method of claim 12, wherein the mutant eIF4E polypeptide consists of the same sequence as the wild-type eIF4E polypeptide, except that it has a substitution at residue 27 of SEQ ID NO: 1 of an acidic amino acid by a neutral amino acid or by a basic amino acid selected from the group consisting of histidine, lysine, and arginine, or by a neutral amino acid selected from the group consisting of alanine, valine, leucine, isoleucine, phenylalanine, methionine, glycine, serine, threonine, tyrosine, cysteine, glutamine, and asparagine.

17. A method for selecting a plant of the family Solanaceae that is resistant to potyvirus infection comprising:

(A) identifying a plant of the family Solanaceae that contains at least one mutation in the wild-type eIF4E polypeptide sequence of SEQ ID NO: 1, and (B) selecting a plant that is resistant to potyvirus infection compared to the wild-type plant;

wherein the wild-type eIF4E polypeptide comprises SEQ ID NO: 1.

18. The method of claim 17, wherein said at least one mutation results a substitution of a neutral amino acid residue at one or more positions selected from the group consisting of positions 2, 3, 4, 5, 7, 9, 10, 11, 12, 13, 14, 15, 16, 18, 19, 20, 21, 22, 23, 24, 25, 28, 29, 30, 31, 32, 33, 34, 35, 38, 39, 41, 42, 43, 44 and 45 in SEQ ID NO: 1 with a charged amino acid residue.

19. The method of claim 17, wherein said mutation is a substitution of at least one neutral amino acid residue in SEQ ID NO: 1 with a charged amino acid residue, wherein said substitution occurs at at least one position selected from the group consisting of position 2, 3, 4, 5, 10, 16, 18, 19, 24, 30, 31, 42 and 43 of SEQ ID NO: 1.

20. The method of claim 17, wherein said plant of the Solanaceae family is a pepper and said mutation is a substitution at residue 4 or residue 16 with a basic amino acid.

21. The method of claim 17, wherein said plant of the Solanaceae family is a tomato and said mutation is a substitution at residue 2 of SEQ ID NO: 1 with a basic amino acid or a substitution of the Ala at position 11 of SEQ ID NO: 1 with an acidic amino acid.

22. The method of claim 17, wherein said at least one mutation results in at least one substitution of a charged amino acid residue at one or more positions selected from the group consisting of positions 1, 6, 8, 17, 26, 27, 36, 37, 40, and 46 in SEQ ID NO: 1 with a neutral amino acid residue or an amino acid residue of the opposite charge.

23. The method of claim 17, wherein said at least one mutation is at least one substitution of a charged amino acid residue in SEQ ID NO: 1 with a neutral amino acid residue or an amino acid residue of the opposite charge at, wherein said substitution occurs at least one position selected from the group consisting of residues 8, 27, and 37 of SEQ ID NO: 1.

24. The method of claim 17, wherein said plant of the Solanaceae family is a pepper and said mutation is a substitution of the acidic Asp residue at residue 46 of SEQ ID NO: 1 with a neutral amino acid.

* * * * *